(12) United States Patent
Campagna

(10) Patent No.: US 11,813,033 B2
(45) Date of Patent: Nov. 14, 2023

(54) MEDICAL IMAGING COMPATIBLE RADIOLUCENT ACTUATION OF TRANSLATION ROTATION ARTICULATION CIRCUMDUCTION JOINT

(71) Applicant: Michael Campagna, Naperville, IL (US)

(72) Inventor: Michael Campagna, Naperville, IL (US)

( * ) Notice: Subject to any disclaimer, the term of this patent is extended or adjusted under 35 U.S.C. 154(b) by 633 days.

(21) Appl. No.: 16/908,620

(22) Filed: Jun. 22, 2020

(65) Prior Publication Data

US 2021/0393353 A1 Dec. 23, 2021

(51) Int. Cl.
| | |
|---|---|
| A61B 34/30 | (2016.01) |
| B25J 15/06 | (2006.01) |
| A61B 34/00 | (2016.01) |
| A61B 90/14 | (2016.01) |
| B25J 9/16 | (2006.01) |
| B25J 9/10 | (2006.01) |
| B25J 9/02 | (2006.01) |
| B25J 9/14 | (2006.01) |
| A61G 13/12 | (2006.01) |

(52) U.S. Cl.
CPC .............. *A61B 34/71* (2016.02); *A61B 34/30* (2016.02); *A61B 90/14* (2016.02); *A61G 13/1265* (2013.01); *B25J 9/02* (2013.01); *B25J 9/101* (2013.01); *B25J 9/104* (2013.01); *B25J 9/142* (2013.01); *B25J 9/1615* (2013.01); *B25J 15/0625* (2013.01)

(58) Field of Classification Search
CPC .......... A61B 34/71; A61B 34/30; B25J 9/142
See application file for complete search history.

(56) References Cited

U.S. PATENT DOCUMENTS

| | | | |
|---|---|---|---|
| 5,596,619 A * | 1/1997 | Carol | A61N 5/01 378/65 |
| 10,259,122 B2 * | 4/2019 | Odhner | B25J 15/024 |
| 2006/0207419 A1 * | 9/2006 | Okazaki | F15B 11/20 91/35 |
| 2012/0053597 A1 * | 3/2012 | Anvari | A61B 34/35 606/130 |
| 2012/0260923 A1 * | 10/2012 | Campagna | A61G 13/0072 128/845 |
| 2013/0000480 A1 * | 1/2013 | Komatsu | B25J 9/1615 92/48 |
| 2013/0158565 A1 * | 6/2013 | Anvari | A61B 90/00 606/130 |

FOREIGN PATENT DOCUMENTS

WO WO-2014028288 A1 * 2/2014 ............. A61B 6/032

* cited by examiner

*Primary Examiner* — Boniface Ngathi
(74) *Attorney, Agent, or Firm* — Addy Hart P.C.

(57) ABSTRACT

A radiolucent circumduction joint that has one, two, or three degrees of axis move movement about a central point that is able to mirror human joint movement.

10 Claims, 18 Drawing Sheets

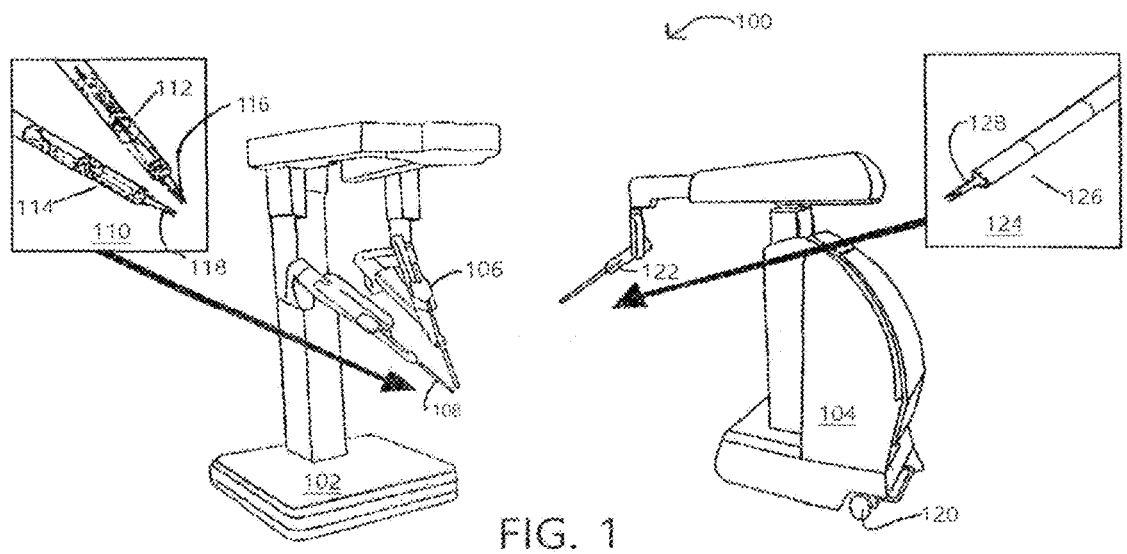
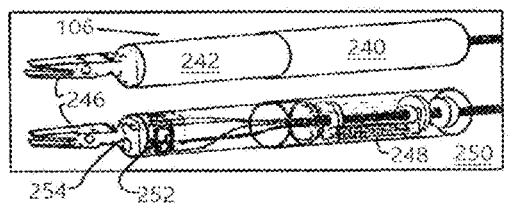
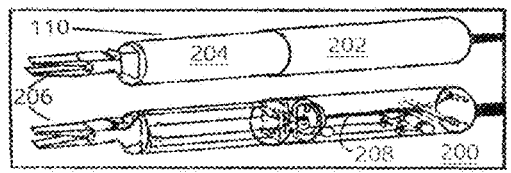
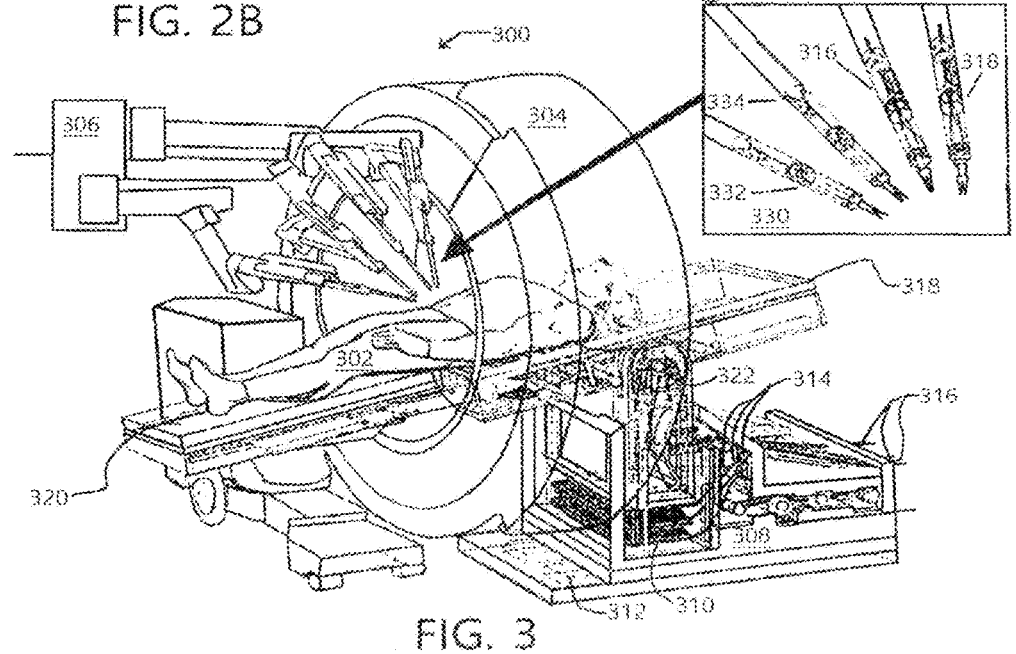
FIG. 1
FIG. 2B
Fig. 2A
FIG. 3

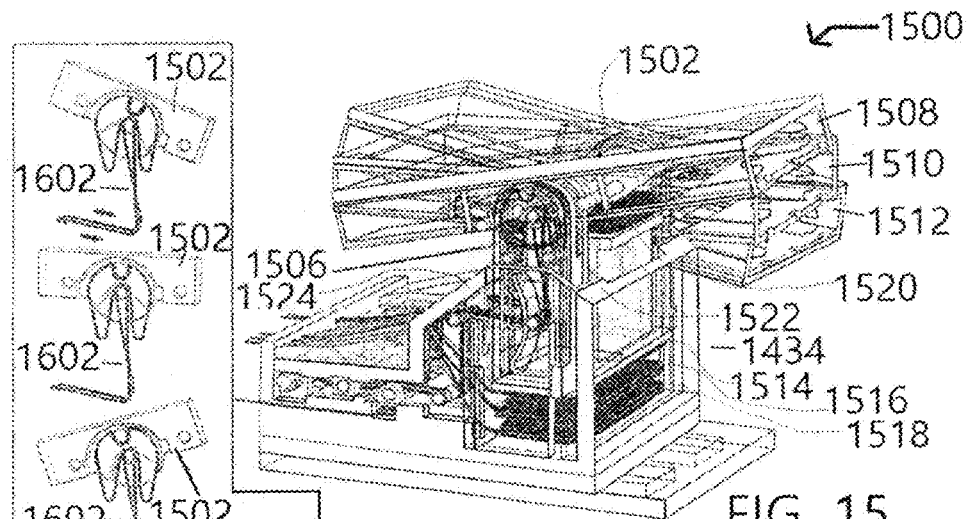
FIG. 15
FIG. 16
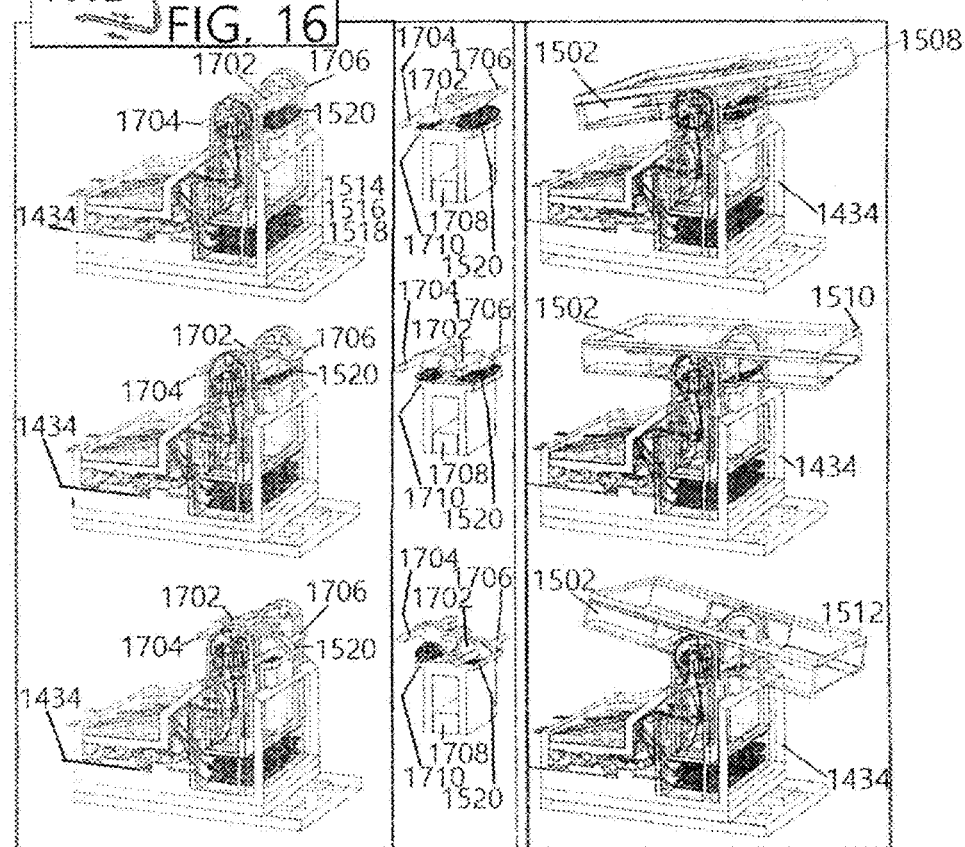
FIG. 17

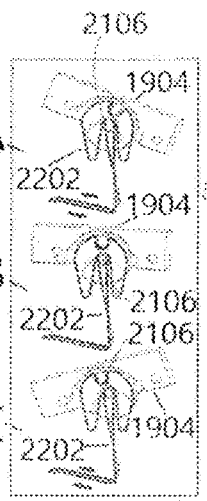
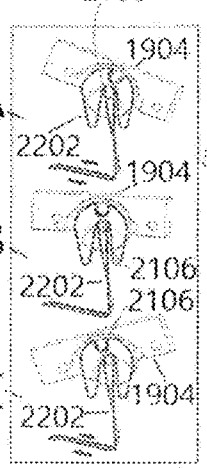
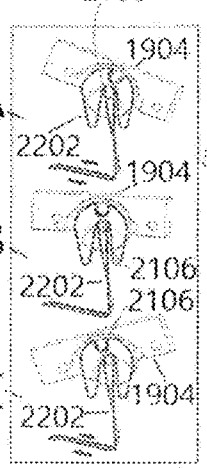
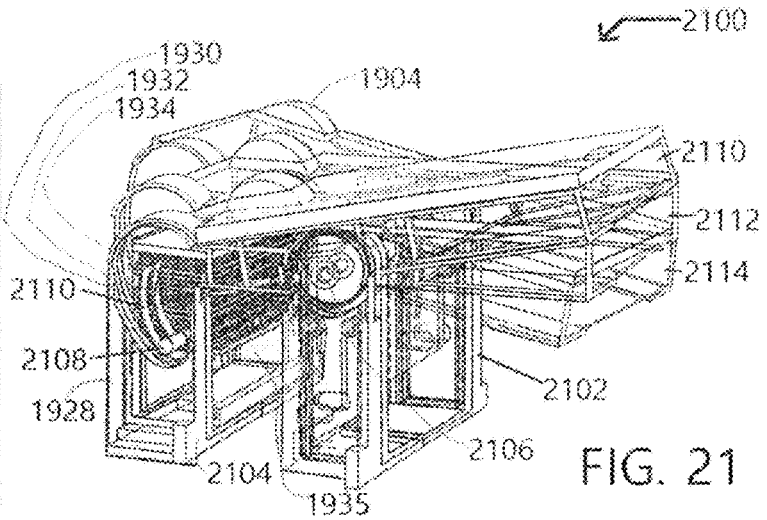
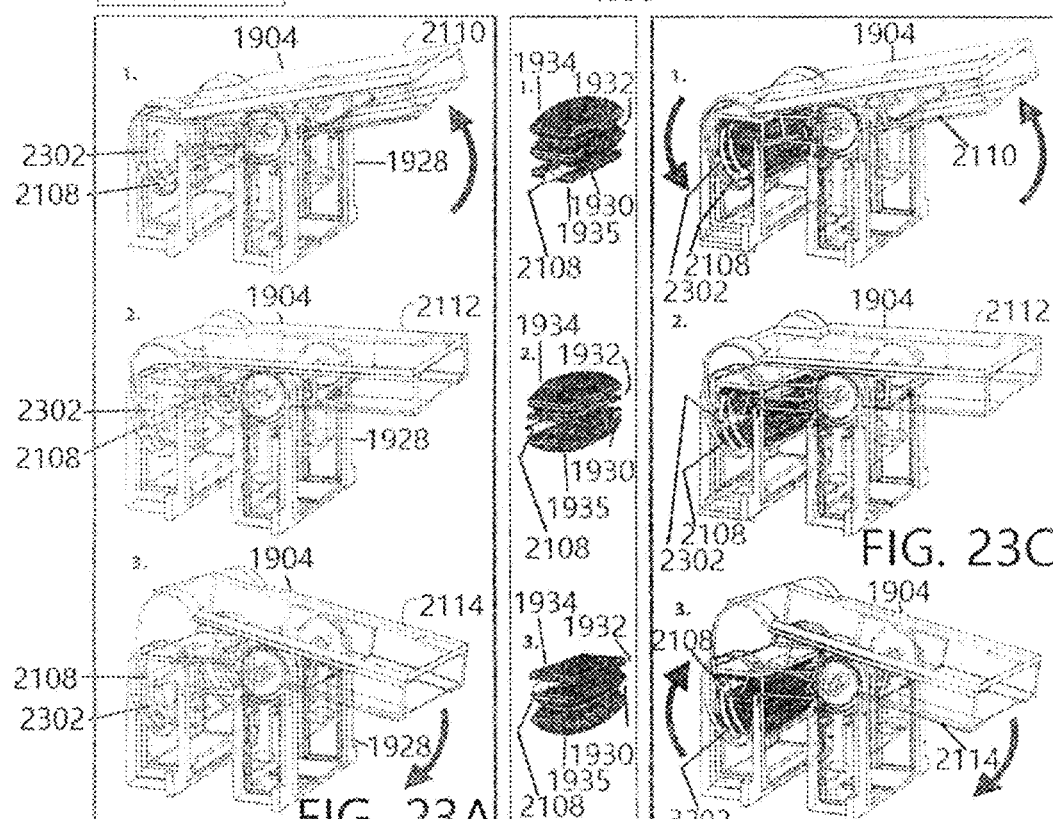
FIG. 22A
FIG. 22B
FIG. 22C
FIG. 21
FIG. 23A
FIG. 23B
FIG. 23C

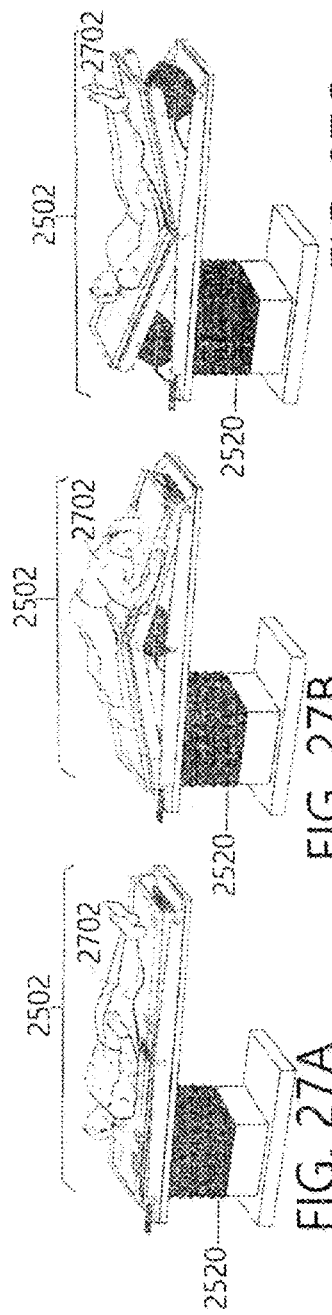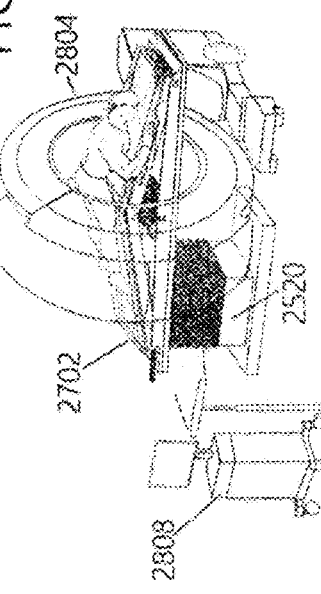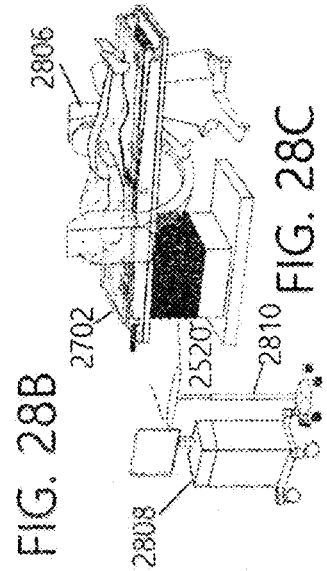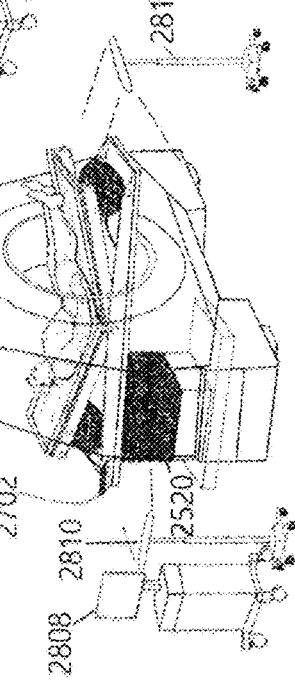

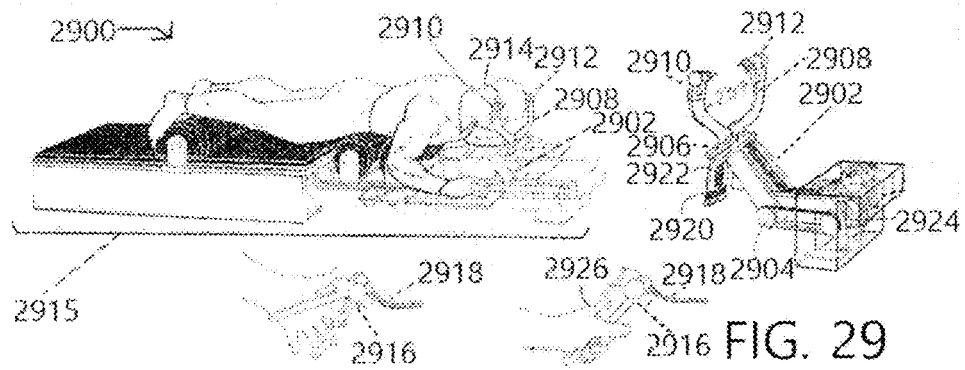
FIG. 29
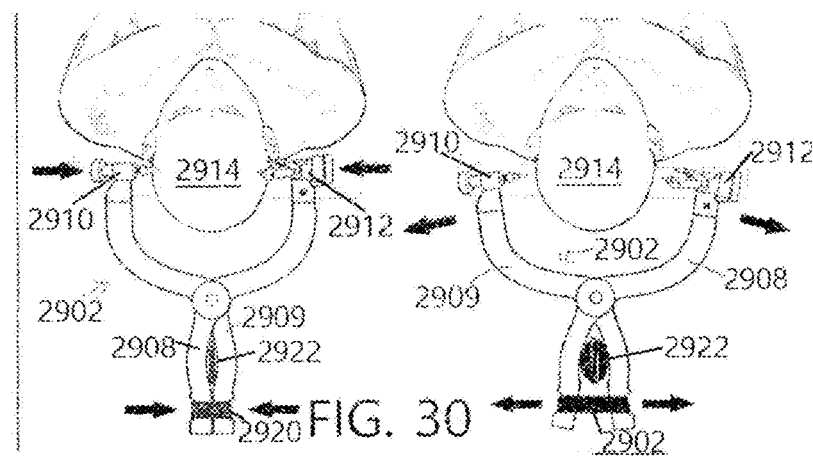
FIG. 30
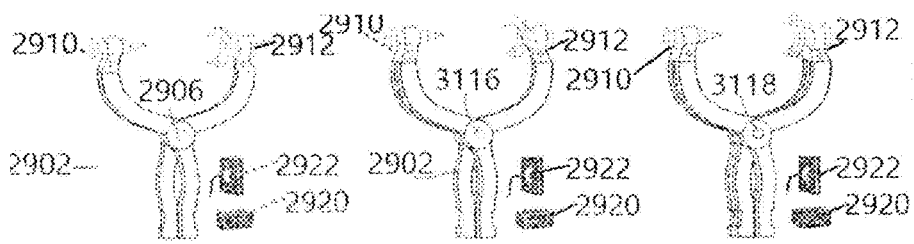
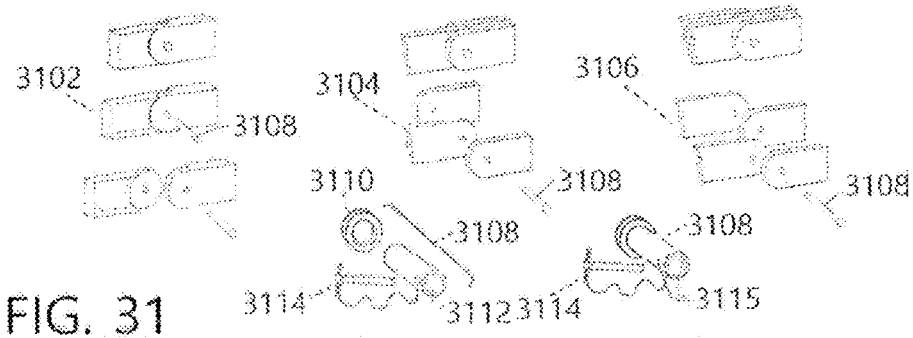
FIG. 31

MEDICAL IMAGING COMPATIBLE RADIOLUCENT ACTUATION OF TRANSLATION ROTATION ARTICULATION CIRCUMDUCTION JOINT

RELATED APPLICATIONS

This application claims priority to U.S. Provisional Patent Application No. 63/038,743, titled "MEDICAL IMAGING COMPATIBLE RADIOLUCENT ACTUATION OF TRANSLATION ROTATION ARTICULATION CIRCUMDUCTION," filed on Jun. 12, 2020, by Michael Campagna and is incorporated by reference in its entirety herein.

This application DOES NOT claim priority to but does incorporate by reference U.S. patent application Ser. No. 13/902,939, titled "ARTICULATING PATIENT POSITIONING APPARATUS," filed on May 27, 2013, by Michael Campagna.

TECHNICAL FIELD

The present invention relates generally to robotics and more particularly to robotic joints.

BACKGROUND

The current technology for robotic arm movement requires electric motors or servos that directly or indirectly (with cables) move and control the joints. Typical robots have joints that are offset or otherwise not in line with their arm portion making it difficult if not impossible to closely mimic human motion. In many currently deployed robots, such as industrial robots, the necessity to mimic human movement is not required. But in robots that are required a high degree of accuracy when performing functions, such as surgery, it is desirable to mimic human motion. By mimicking motion, a more natural and intuitive control system may be employed to operate or otherwise move a robotic limb. The current surgical robots are unable to closely mimic human motion making control systems for such robots more complicated and less accurate.

Similarly, current approaches require cables or other members to move joints that are not radiolucent. Such joints, therefore, can create problems and limitations on positioning in addition to the mechanical limitations that have already been described.

Therefore, there exists a need in the field of robotic limb manipulation to have a robotic joint that enables robotic arms to more precisely mimic human motion.

SUMMARY

By using thin radiolucent laminar sheeting as the basic building blocks of the one, two, and three degrees of freedom joints and structures, and via the utilization of the most radiolucent material known, essentially invisible air and inert medical gas for pneumatic actuation, with the implementation of non-metallic cable as further means of manipulation and braking, hollow, and yet strong articulating mechanism may be created. Examples of such mechanism include, without limitation, patient platforms, anatomic positioners, surgical robotics, and circumduction end effectors, as well as other essential mechanisms that make use of articulated medically imaging compatible radiolucent armatures for the placement and manipulation of surgical operating microscopy, surgical retraction devices, and image guidance arrays that are enabled to be operable entirely within the medical imaging environment with minimal density or high attenuation artifacts and thereby functioning in ways which neither significantly affect the quality of the diagnostic information nor have its operations affected by the medical imaging systems.

Furthermore, via the usage of solenoid manifold computer coordinated command and control of instantaneous spatial positioning feedback derived from energy reflective fiducials placed strategically on key points of the Structures of the Present Invention situated within a live medical imaging environment, all of these said devices are enabled to be remotely operable from outside of the live medical imaging environment in ways which neither significantly affect the quality of the diagnostic information nor have its operations affected by the medical imaging system."

By using radiolucent laminar sheeting as the basic building blocks of a one, two, and three degrees of freedom joints and structures, and via the utilization of the most radiolucent material known, essentially air and/or inert medical gas as inflation material for pneumatic actuation, with the implementation of non-metallic cable as a further approach for of manipulation and braking. Approaches for the creation of essentially, hollow, and yet very strong articulating mechanisms of this laminar sheeting, to include without limitation, patient platforms, anatomic positioners, surgical robotics, and circumduction end effectors, as well as other mechanisms to include articulated medically imaging compatible radiolucent armatures for the placement and manipulation of surgical operating microscopy, surgical retraction devices, and image guidance arrays without limitation, all enabled to be operable entirely within the medical imaging environment with minimal density or high attenuation artifact and thereby functioning in ways which neither significantly affect the quality of the diagnostic information nor have its operations affected by the medical imaging system.

The apparatus of the present invention also introduces medically imaging compatible, radiolucent approach for spatial management, command, and control of the actuation/rotation of the radiolucent one, two, and three degrees of freedom rotatable joints via utilizing solenoid manifold coordination of the inverse proportional, inflation and deflation of radiolucent pneumatic antagonistic flexor extensor inflation cells upon the substantially rhomboidal/Lozenge shaped effort arm(s) and lifting pole(s) as actuators of the radiolucent rotatable joints.

Other devices, apparatus, systems, methods, features, and advantages of the invention will be or will become apparent to one with skill in the art upon examination of the following figures and detailed description. It is intended that all such additional systems, methods, features, and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 1 depicts a diagram of a surgical robot having pneumatic bags in accordance with an example implementation of the invention.

FIG. 2A depicts a cutaway view of the cable-actuated surgical robot's lower arm of FIG. 1, controlled with cables and radiolucent joints in accordance with an example implementation.

FIG. 2B depicts a cutaway view of the pneumatic inflation actuated surgical robot's lower arm of FIG. 1, controlled with pneumatic bags in accordance with an example implementation.

FIG. 3 depicts the surgical robot with the surgical robot's lower arm similar to FIG. 2B as would be used on a patient within an MM imager and radiolucent imaging compatible surgical table controlled by pneumatic bags in accordance with an example implementation of the invention.

FIG. 15 is an illustration of the support structure and base of FIG. 14 depicting the tilting of the support structure in accordance with the example implementation of the invention.

FIG. 16 illustrates a radiolucent cable braking mechanism of FIG. 15 in accordance with and example implementations.

FIG. 17 depicts how the tilting of the support structure of FIG. 15 is accomplished with a pair of pneumatic bags in accordance with an example implementation of the invention.

FIG. 21 is an illustration of the radiolucent dual pylon member 1928 of FIG. 19 in accordance with an example implementation of the invention.

FIGS. 22A-C illustrates the radiolucent cable braking mechanism for the surgical table of FIG. 19 in accordance with an example implementation of the invention.

FIGS. 23A-C illustrates the position of the radiolucent load-lifting pole of FIG. 21 with bearings and its effect on the positioning of the one-piece tabletop housing in accordance with an example implementation of the invention.

FIGS. 27A-C illustrates the radiolucent imaging compatible flexion/extension spine table retro-fit top, utilizing one degree of freedom radiolucent flexion/extension hinge of FIGS. 25 and 26 with a patient in different positions in accordance with an example implementation.

FIGS. 28A-C illustrates the radiolucent imaging compatible flexion/extension spine table retro-fit top, utilizing one degree of freedom radiolucent flexion/extension hinge of FIGS. 25, 26, and 27 with imaging devices and computer-assisted guidance system in accordance with an example implementation of the invention.

FIG. 29 depicts a pneumatically actuated radiolucent skull clamp utilizing rotatable radiolucent hinge joints comprised of laminar sheeting that enable greater surgeon control of verifiable clamp force to the skull that is part of a surgical table similar in operation to the surgical table of FIG. 3 and clamp hand controller in accordance with an example implementation of the invention.

FIG. 30 depicts the operation of the radiolucent skull claim of FIG. 29 in accordance with the example implementation of the invention.

FIG. 31 illustrates the joints and the laminar sheeting that make up the radiolucent skull clamp in accordance with the example implementation of the invention.

DETAILED DESCRIPTION

Figure 4:
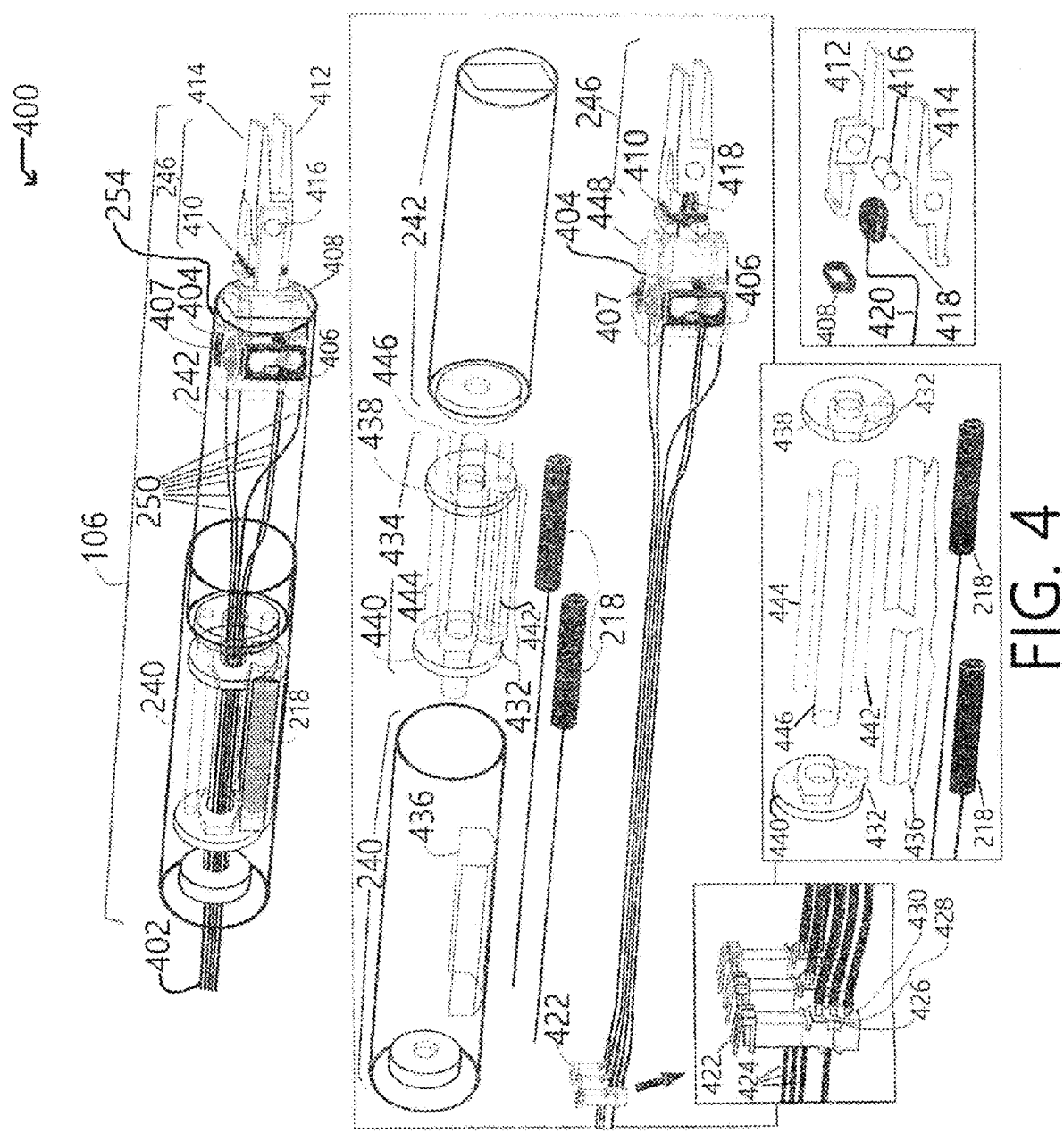
FIG. 4 illustrates the lower arm of FIG. 2B that identifies the major components in accordance with the example implementation of the invention.

An approach for manipulating joints in a surgical robot using inflatable bags that may be inflated using gas or liquids depending upon the implementation. Furthermore, all or some of the joints may be controlled using the disclosed approach.

Turning to FIG. 1, a diagram 100 of a surgical robots 102 and 104 having pneumatic bags is depicted in accordance with an example implementation of the invention. Surgical robot 102 is shown as being non-mobile with more than one mechanical arm, arms 106 and 108 in the current example implementation. The ends 112 and 114 of mechanical arms 106 and 108 respectively are depicted in cut-away views in window 110 of FIG. 1. As seen in window 110 the ends of the mechanical arms 106 and 108 can move in and out and the end effector (116 and 118) or instrument end can have movement to open and close an instrument in addition to being rotatable in the current example. In other implementations, other types of movements may be employed, including joints, cable controlled flexing, or other known types of robotic limb movements.

Surgical robot 104 of FIG. 1 is a mobile surgical robot having wheels 120 and can be moved or otherwise relocated within an operating room or facility. Surgical robot 10 is depicted with one robotic arm 122 that has a lower end 126 shown in a blowup view in window 124. The lower end 126 can move in and out and has an end effector or tool end 128.

Turning to FIG. 2A, a cutaway view 200 of the cable-actuated surgical robot's 102 lower arm 114 of FIG. 1, controlled with cables and having radiolucent joints and bags used to control the end effector 206 is depicted in accordance with the example implementation. The end effector 206 is coupled to The cables enables the rotation of the end effector 206 and the moving in and out of part 204 relative to part 202 of the lower arm 114 of FIG. 1.

In FIG. 2B, a cutaway view 250 of the pneumatic inflation actuated surgical robot's lower arm 106 of FIG. 1, controlled with pneumatic bags 248 and 252 controlling a radiolucent joint in accordance with the example implementation. The pneumatically actuated medically imaging compatible rotatable radiolucent joint. Joints may be created to be a uni-axial one degree of freedom flexion/extension joint, or as a uni-axial one degree of freedom abduction/adduction radiolucent joint, or as a biaxial two degrees of freedom circumduction joint, or as a tri-axial three degrees of freedom laterally rotatable circumduction joint, thru the implementation of one pneumatic flexor/extensor antagonistic pair per each substantially rhomboidal effort arm, and each degree of freedom. For example, a uni-axial joint having one pneumatic flexor/extensor antagonistic pair of pneumatic bags for the one degree of freedom rotation of one substantially rhomboidal effort arm of laminar sheeting, the biaxial joint having two separate pneumatic flexor/extensor antagonistic pneumatic bag pairs for the two separate degrees of freedom rotation of the two substantially rhomboidal effort arms of radiolucent laminar sheeting, and the tri-axial joint having three pneumatic flexor/extensor antagonistic pneumatic bag pairs for the three separate degrees of freedom rotation of the three substantially rhomboidal effort arms of laminar sheeting. It is noted in the current implementation that with all of the described degrees of freedom, they are rotatable around only one central pivot point of a radiolucent joint.

The filling and emptying of the radiolucent pneumatic bags 248 control the extension joint's rotational motion of the lower arm 106 portion 242 relative to portion 240. The bag 248 in the current implementation is a pair of bags that work inversely together. As one fills the other releases their contents (be it air, other gas, or liquid). In the current implementation, a non-fero magnetic solenoid is used to effectuate the filling or emptying of the bags. In some implementations, a magnetic solenoid can be employed where the magnets will not compromise image integrity, whereas in MRI usage, a hydraulically actuated non-fero magnetic solenoid may be used. Similarly, bag 252 controls some of the motion of the end effector XYZ circumduction hub 254 (wrist joint) with additional pneumatic bags controlling the opening and closing of the end effector 246 or tool end of the lower arm 106. The bag 252 in the current implementations is also a pair of bags that work inversely together acting on a rhomboidal effort arm (rhomboidal effort arm is a generally shaped rhomboidal member that include a leaf shaped rhomboidal member). In other implementations, a single pneumatic bag approach is employed, the joint is biased in one direction by mechanical means, such as a spring, cylinder, stretchable band, or similar device, and the filling and emptying of the pneumatic bag result in movement of the joint or member that is biased. Thus, by using pneumatic bags to impart a force on or otherwise move joints an advantage over the prior art is achieved with a more reliable device having fewer moving parts (since cables are not used for movement) than a traditional surgical or manufacturing robotic arm. A further advantage of using inflation and deflation of one or more pneumatic bags in a robotic arm is the ability to have the pneumatic bags internal to the robotic arm enabling robotic arm joints and/or movement to more closely mimic human arm/wrist/hand/finger movements.

In summary, the surgical robot's lower arm 106 has a pneumatically actuated three degrees of freedom that are radiolucent rotatable, rotational, circumduction acting on the end effector joint 246, utilizing XYZ Hub 254, enabling flexion and extension in the vertical plane, abduction and adduction in the horizontal plane, the combination all of these said joint movements as the circumduction function, and also enabling lateral rotation of the entire XYZ hub circumduction hub 254, such that the End Effector 246 is enabled to replicate the rotational and circumduction functions of the human wrist due to the convergence of all rotational axes and rotation at the one central pivot point at the circumduction hub 254.

The essential principles at work within the design characteristics of radiolucent pneumatic bags (inflation cell) that are utilized as pneumatic lifting and flexor extensor inflation cells require their construction from materials that exhibit both strength and elasticity. Essentially, in order to preserve non-metallic, radiolucent functionality of any portion of the inflation cell that is to be utilized within the imaging bores such inflation cells will be constructed to be inherently connected to the tubing which supplies the ingress and egress gases via Schrader, Presta Style or Dunlop valves or adaptors which attach to the solenoid or solenoid flow control valve or solenoid flow control manifold. Thereby, through inherent construction of the gas supply tubing and the inflation cell as one piece, or through the fusion of the tubing and the inflation cell into one piece, the portions of the inflation cell and hose or tubing which is within the imaging bore may remain metal and therefore artifact-free, necessitating then that the (Metal) Schraeder, Presta or Dunlop style valves or adaptors may then be located at the furthest point of the tubing away from the inflation cell, thereby enabling the Schrader, Presta or Dunlop Valves to be inserted into the solenoid manifold or the pressure control/gas flow control system while outside of the Imaging Bore, and thereby eliminating Artifact from within the imaging bore. Construction of the larger radiolucent pneumatic bags (inflation cells), utilized for substantial load-bearing and vertical translation of the patient support structures and equipment load-bearing structures, as well as for inflation cells utilized within the one and two degree and three degrees of freedom hubs which move equipment and portions of the anatomy, the preferred means of inflation cell construction will be similar to that used in rescue bags utilized by fire departments in order to move heavy rubble or large structures during rescue procedures. Such rescue bags are constructed primarily from Neoprene and Kevlar, and these materials, without limitation, being low density and thereby essentially radiolucent, are excellent materials for the construction of said lifting cells. In addition to Kevlar, Zylon or ABC-matrix for load-bearing strength may be used, such inflation cells may also be constructed without limitation, from the group of materials to include silicone rubber, neoprene rubber, EPDM, Viton, Natural Rubber, Nitrile Rubber, Butyl Rubber, Timprene, Synthetic Rubber, Flexible PVC, TPE Thermoplastic Elastomers, as well as from other similar elastic materials as are presently being developed. The elasticity and load-bearing strength are the essential properties necessary for the function of such larger load-bearing inflation cells in addition to radiolucency in some implementations.

For the smaller radiolucent pneumatic bags (inflation Cells), utilized as flexor extensors within radiolucent robotic end-effectors and radiolucent surgical end effectors, which will of necessity, be inserted within the human body during surgical procedures, there is a basic similarity between such inflation cells and the so-called "inflation cuffs" within Endo Tracheal cuffs and tubing. As such, there exists then readily identifiable materials from which such small inflation cells and tubing may be selected, without limitation from the following group of Bio-compatible elastic materials currently utilized in endotracheal cuffs and tubing, to include Urethane, Polyurethane like quadruplex, polycarbonate urethanes like quadrathane, silicones and thermoplastic silicones, quadrasil, polyvinyl chlorides, aliphatic polyetherm based thermoplastic polyurethanes, and other similar elastic biocompatible materials as are presently being developed. The elasticity and biocompatibility are the essential properties necessary for the function of such small inflation cells.

It is noted that a dedicated and reusable device may also be configured utilizing primarily silicone-based materials which exhibit both excellent durability, elasticity, as well as biocompatibility, and also withstand the high heat of steam sterilization as well as the fact that peroxide cured silicone is compatible with ETO ethylene oxide sterilization protocols with no degradation of either structure or characteristics, as well as silicone being compatible with Gamma Sterilization and Sterrad Hydrogen Peroxide Sterilization.

Alternately, an embodiment of said surgical end effectors, the inflation cells and tubing of the present invention may be supplied in a single usage disposable cartridge form, which may be readily inserted into the effort arm of the surgical robotic unit with an end effector, said cartridge both readily and easily connected to a dedicated and reusable air tube within the robotic arm, and then the cartridge containing the inflation cells and tubing may be disconnected and discarded after each surgical usage.

Such a disposable end effector may also include the usage of non-metallic End Effector Tools, with tiny amounts of non-metallic yet high atomic weight material being incorporated at the very tip of the end effector as tracking fiducials, thereby enabling full usage of the end effector during live imaging, without introducing metals, and via the introduction of only the most minute traces of high attention materials for purposes of Pinpoint Location of the end effector via imaging.

Turning to FIG. 3, a surgical robot 306 with the surgical robot's lower arms 332, 334, 335, and 338 similar to FIG. 2B as would be used on a patient 302 within a movable MRI imager or more precisely a Medtronic O-arm of a live imaging bore 304 and a surgical table 308 controlled by pneumatic bags 310 is depicted in accordance with an example implementation of the invention. As shown, the lower arms 332, 334, 335, and 338 may extend into the O-arm 304 while being used. But, since the arms of the surgical robot 306, including the lower arms 332, 334, 335, and 338 and joints are made out of radiolucent material including laminar sheeting material they can extend into the O-arm 304 with minimal impact on the imaging.

The surgical table 308 is depicted with mechanical means, such as electrical motor, pneumatic cylinder, bags, or similar devices to move the surgical table upon a track 312. A pair of pneumatic bags 310 are depicted with hoses 314 that enable the bags to be deflated or inflated with a material; air, gas, and/or liquid, or a combination of air, gas, and/or liquid depending upon the implementation. The inflation of the pneumatic bags 310 raises the surgical tabletop 318 with the patient 302 sitting on the patient support 320. In the current example, the bags described in this document may be inflated with compressed air, oxygen, nitrogen, or other inert gas, with oxygen or nitrogen being the preferred gas in the current example because it is readily available in medical facilities. Each pneumatic bag may have a separate hose connected to a solenoid manifold controlled by non-ferromagnetic solenoids for inflation and deflation. The surgical table is configured and radiolucent pneumatic hoses/radiolucent cables routed in some implementations to enable the surgical table to be transported with a lift jack while in use, enabling a patient to be moved into and out of an imager while on the surgical table. In other implementations, each pneumatic bag may share the same hose depending upon the implementation. In yet other implementations, each pneumatic bag may share a common exhaust line with each pneumatic bag being independently exhaustible. The substance (gas, liquid, gel, or other substance) to inflate/deflate a pneumatic bag may be pumped into the bag or injected into the pneumatic bag with pressure, such as pressurized air from a gas cylinder and controlled by a solenoid manifold. In other implementations, each pneumatic bag may have one or more valves located at the pneumatic bag controlled electronically, mechanically, or electromechanically that facilitates filling and emptying the pneumatic bag. In the current implementations, connections for electrical and air 316 are shown exiting the table and are connected to connections receptacle and spigots built into the walls of the room (not shown). In emergencies, disasters, military deployment, or third world usage, some or all of the bags may be configurable to be inflated with either hand or foot pumps, squeeze pumps, or simple plunger style/string style pumps.

The patient support 320 can extend in and out from the surgical tabletop 318. The movement of the patient support 320 allows a patient to be moved within the MRI scanner and is preferably made out of radiolucent material. The surgical tabletop 318 is pivotally mounted on an axil assembly 322 that is depicted as having the orientation of the surgical tabletop 318 controlled via pneumatic bags with the inflation and deflation of one or more pneumatic bags controlling the rotation of the surgical tabletop 318. The axil assembly 322 in the current implementation is made out of radiolucent material and preferably radiolucent laminar sheeting material, but in other surgical implementations it may be irrelevant if it is or is not made out of radiolucent material. In other implementations, cables may be employed. In yet other implementations, a combination of pneumatic bags and cables may be employed. The surgical table 318 is also depicted with the ability to be raised and lowered the surgical tabletop 318 along with the axil assembly 322 using pneumatic bags 310.

In FIG. 4, an illustration 400 of the major components of the lower arm 106 of FIG. 2B is shown in accordance with the example implementation of the invention. The lower arm 106 has rotational portions 242 that rotates relative to portion 240 with the inflation and deflation of one or more pneumatic bags 218 (i.e. lateral rotational antagonistic flexor inflation cell). If a single pneumatic bag approach is used, the rotatable lower arm portion 242 is biased in a non-rotated position with the use of a biasing means, such as springs, stretchable ring, pistons, or other such material. It is preferred that material for the biasing means be radiolucent. For the lower arm portion 242 to rotate relative to the lower arm portion 240, one or more pneumatic bags 218 are inflated using one or more hoses/pressurized gas lines 402. It is preferable to route the hoses/pressurized gas lines 402 through the center axis of the lower portions 240 and 242 to prevent binding and assure access to the different pneumatic bag locations 250 in the lower arm 106. The inflation of the pneumatic bag acts upon a lower arm rhomboidal effort arm 432.

An effort arm assembly 434 for lateral rotation of the lower arm portion 242 is coupled to the lower arm portion 242 and resides in lower arm portion 240. An inflation chamber for the lateral rotational inflection cell or pneumatic bag 434 supports one or more pneumatic bags 218 between the two ends 438 and 440 of the effort arm assembly 434. Stability of the effort arm assembly 434 is maintained with upper and lower rotational pole supports 442 and 444 that extend between and are affixed to the two ends 438 and 440, which rotate via the inflation of the pneumatic bag(s). An inflation line tube 446 lies along the center axis of the effort arm assembly 434 is provides a raceway for hoses/pressurized gas lines through the center of the effort arm assembly 434.

In the lower arm portion 242, a circumduction hub/wrist joint 404 is depicted. The wrist joint 404 is composed of radiolucent material, preferably radiolucent laminar sheeting and part of the wrist joint 404 with a circumduction hub rhomboidal effort arm held steady between two opposing pneumatic bags 406 and 407. In other implementations, the wrist joint may be biased by one or more biasing means and one or more pneumatic bags may control the movement of the biased wrist joint. In yet other implementations, pneumatic bags may be used in other lower arm joints and cables used to control the wrist joint 404.

An end effector 246 is depicted in the current implementation as having two opposing grippers 412 and 414 pivotally connected with a pin 416 and biased in an open position by a radiolucent tension band 410. A single pneumatic bag 418 is inflated and deflated to open and close the grippers 412 and 414 that make up the end effector 246. A hose/pressurized gas line carries gas to inflate and deflate the pneumatic bag 418 in response to the actions of a non-ferromagnetic solenoid manifold 422.

In the current example, the non-ferromagnetic solenoid manifold 422 enables gas to enter the solenoid manifold on one side 424 via hoses/pressurized gas lines and hoses/pressurized gas lines to inflate and deflate pneumatic bags 426-430. In other implementations, other types of solenoids may be employed. In yet other implementations, other types of known inflation and deflation approaches may be employed including microvalves, servo valves, depending upon the pneumatic bag implementation.

Figure 5:
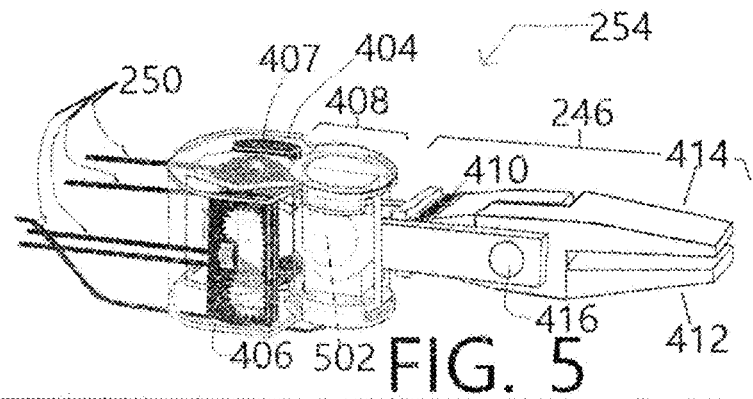
FIG. 5 illustrates the end effector and circumduction hub/wrist of FIG. 2B that are enabled to have a pneumatically actuated three degrees of freedom that are radiolucent rotatable, rotational, circumduction acting on the end effector joint in accordance with the example implementation of the invention.

Turning to FIG. 5, a pneumatically actuated three degrees of freedom that are radiolucent rotatable, rotational, circumduction acting on the end effector joint 246, utilizing the circumduction hub 254, enabling flexion and extension in the vertical plane, abduction, and adduction in the horizontal plane, the combination all of these said joint movements as the circumduction function, and also enabling lateral rotation of the entire circumduction hub 254, such that the end effector 246 is enabled to replicate the rotational and circumduction functions of the human wrist due to the convergence of all rotational axes and rotation at the one central pivot point 502 for all XYZ axes at the circumduction hub 254.

Figure 6:
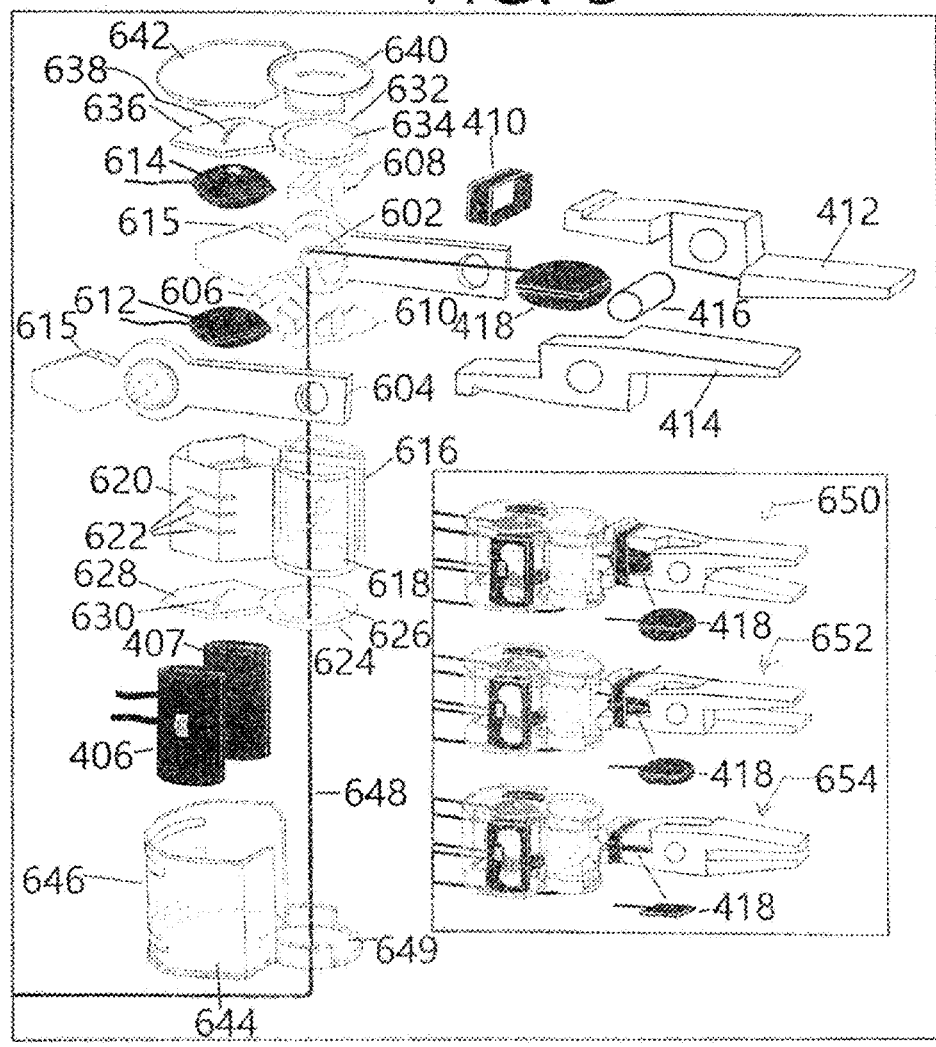
FIG. 6 is an exploded view of the end effector and circumduction hub/wrist of FIG. 2B and FIG. 5 in accordance with an example implementation of the invention.

In FIG. 6, an exploded view of the end effector 246 and circumduction hub/wrist 408 of FIG. 2B and FIG. 5 in accordance with an example implementation of the invention. The lower jaw 412 is pivotally connected to the upper jaw 414 by an axel 416 (i.e. rod, pin, bolt) made from non-metallic material that is preferably radiolucent. A biasing band 410 also preferably made out of non-metallic radiolucent material in the current implementation, is used to bias the lower jaw 412 and upper jaw 414 in a closed position. An end effector pneumatic bag 418 is placed between the lower jaw 412 and upper jaw 414 such that when it is deflated the jaws 412 and 414 are closed. The axel 416 extends through two rhomboidal vertical effort arms 602 and 604. A vertical effort pin 606 couples the two rhomboidal vertical effort arms 602 and 604 together are is further positioned on non-metallic bearing-lined guides 608, 610 that support vertical rotation of the rhomboidal vertical effort arms 602 and 604. Non-metallic, imaging compatible, radiolucent bearings, and other non-laminar sheeting radiolucent parts, which may be comprised (without limitation) from the following materials . . . ceramic, Acetal, Nylon, PTFE, Polymide, Polysulfone, Polyphenylene, Carbon-Graphite, Graphitar™, Oilon-80™, Rulon™, as well as other suitable radiolucent materials. A pair of pneumatic vertical effort arms bags 612 and 614 are positioned to act on the rhomboidal edges of the rhomboidal vertical effort arms 602 and 604. The rhomboidal edges are coated or otherwise covered, at least partially, with non-metallic, imaging compatible, radiolucent bearing material 615. The vertical effort pin 606 also intersects and is held by the female buttress members 616 and 618. Enclosed within the female buttress members are the rhomboidal vertical effort arms 602 and 604 along with the pneumatic vertical effort arms bags 612 and 614. The inner and outer surface of the rhomboidal trolley portion 620 (second support) formed by female buttress members 616 and 618 (first support) is depicted as being at least partially covered with non-metallic, imaging compatible, radiolucent bearing material 622. An inferior platform/bottom horizontal rotational surface 624 that has a horizontal turntable bearing 626 and with one end having a rhomboidal shape 628, where the one end having the rhomboidal shape 628 being at least partially covered with non-metallic, imaging compatible, radiolucent bearing material 630. The inferior platform bottom horizontal rotational surface 624 is fixed in place under the female buttress members 616 and 618.

Similarly, the superior platform/top horizontal rotational surface platform 632 has a turntable bearing 634 and a rhomboidal shape surface 636, where the one end having the rhomboidal shape 628 being at least partially covered with non-metallic, imaging compatible, radiolucent bearing material 638 that sits on top of the female buttress members 616 and 618. That assembly then sits on an inferior surface 644 of a defined rhomboidal rotation inflation cavity 646 (third support) that has semi-circular guides for horizontal rotation 648. Two pneumatic bags reside within the rhomboidal rotation inflation cavity 646 and act on the rhomboidal trolley portion 620 to enable horizontal movement to the joint. A similar superior surface 642 caps the rhomboidal rotation inflation cavity 646 and has semi-circular guides for horizontal rotation 640.

Figure 7:
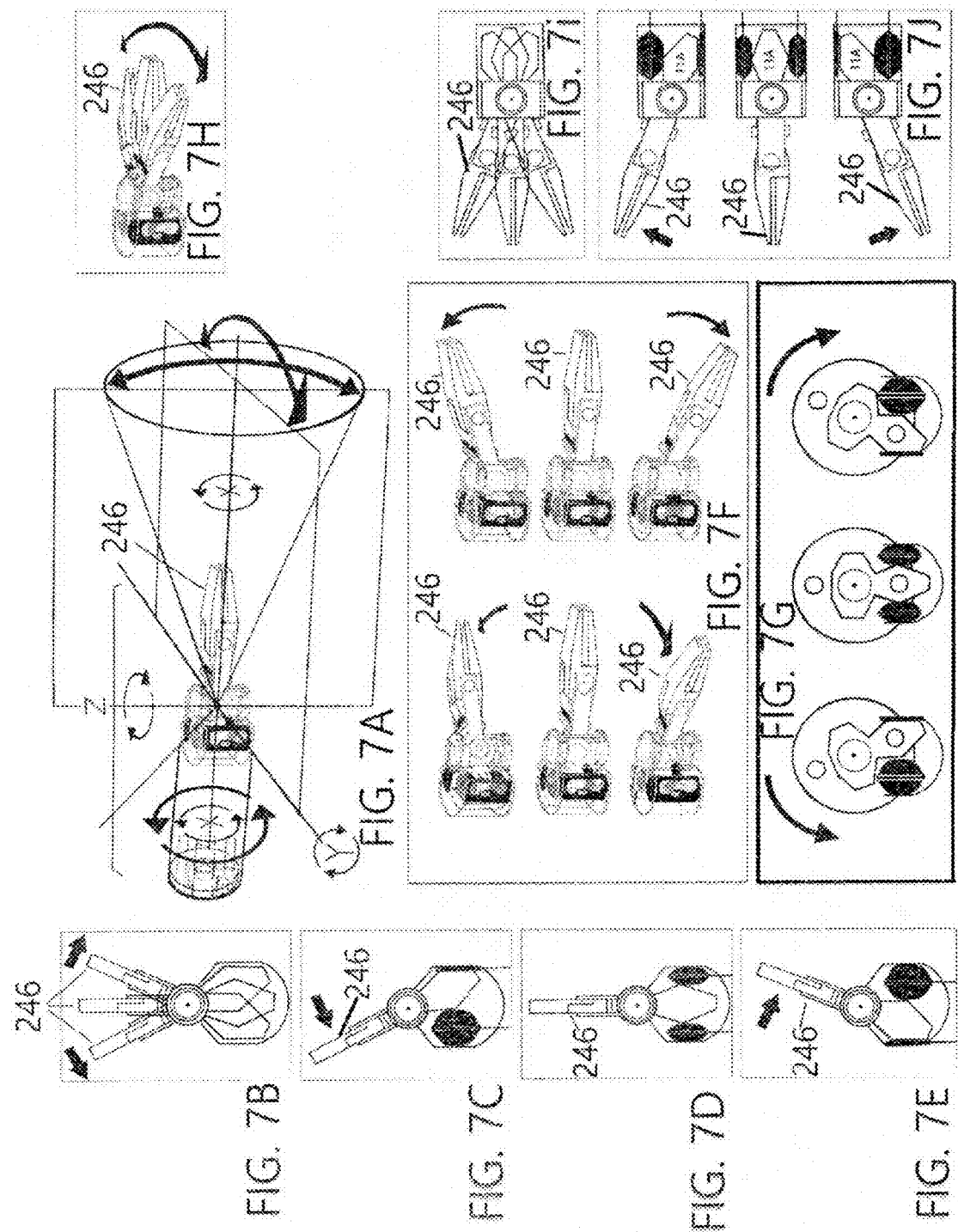
FIGS. 7A-J are diagrams that depict the different positions and movements of the end effector of FIG. 6 in accordance with an example implementation of the invention.

Turning to FIGS. 7A-J, diagrams depict the different positions and movements of the end effector 246. FIG. 7A illustrates the central rotation point of the three-axis X, Y, and Z of the joint that mimics the human wrist. Of note, in FIGS. 7C-G and K, is where the advantage of using a rhomboidal shaped member acting with pneumatic bags can be seen. As one pneumatic bag is inflated, the other is deflated ultimately providing a flat surface for the pneumatic bag to push against while sandwiching the deflated pneumatic bag with a flat surface. Other non-rhomboidal shapes are less desirable because the deflated pneumatic bag may be poked with edges and similarly the fully inflated pneumatic bag may be poked with edges. It is undesirable to be poking the pneumatic bags and could lead to premature failure.

Figure 8:
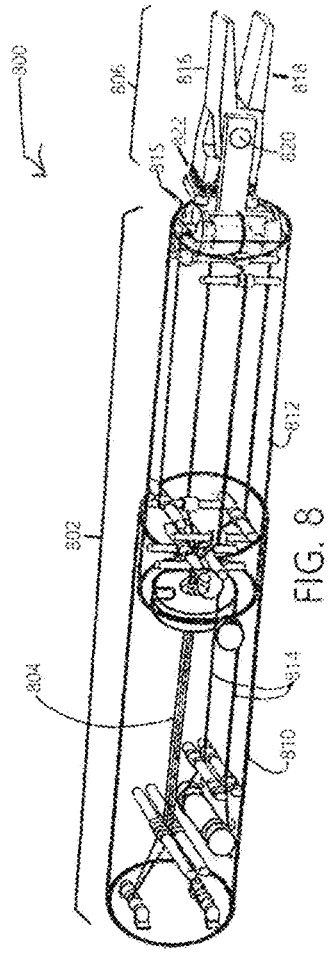
FIG. 8 is a diagrammatic lateral transparent view of a radiolucent imaging compatible assembled robotic arm with three degrees of freedom radiolucent cable actuated end effector similar to FIG. 6 in accordance with an example implementation of the invention.
Figure 9:
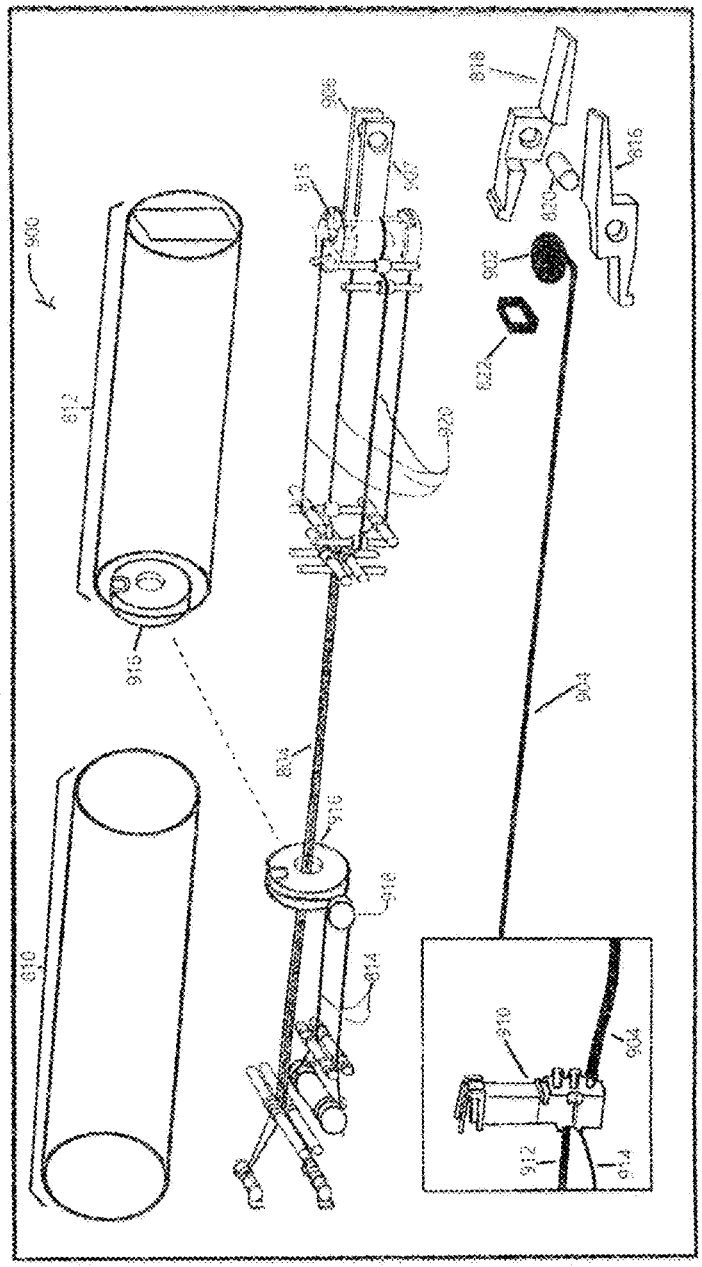
FIG. 9 is a diagrammatic lateral exploded view of the three degrees of freedom radiolucent rotatable, rotational cable actuated robotic arm with an end effector utilizing circumduction joint/XYZ turnable hub of FIG. 8 in accordance with an example implementation of the invention.

In FIG. 8, a diagrammatic lateral transparent view 800 of a radiolucent imaging compatible assembled robotic arm 802 with three degrees of freedom radiolucent cable 804 actuated end effector 806 similar to FIG. 6 is depicted in accordance with an example implementation of the invention. The rotation of an upper robotic arm portion 810 relative to lower robotic arm portion 812 enables the first degree of motion. The motion is controlled by a plurality of cables 814. In the current implementations, the cables are radiolucent cables. A wrist assembly 816 (also called an XYZ turnable hub) is preferably made from radiolucent material, including radiolucent laminate, and is controlled by a plurality of cables 804 to impart a second degree of motion and is also able to move the end effector 806 up and down imparting the third degree of motion that is also controlled by the plurality of cables 804. The end effector 806 has an upper gripper 806, lower gripper 818 that are pivotally connected by a pin 820 in the current implementation. In other implementations, other known pivotal connectors may be employed, such as a bolt, screw, dowel, etc. . . . . The upper and lower grippers 816 and 818 are preferable made out of radiolucent material. The end effector 806 is biased in the closed position by a radiolucent band 822 in the closed position. An inflatable radiolucent pneumatic bag 902, FIG. 9 is inflated to open the end effector 806 and deflated to close the end effector 806 via hose 904, FIG. 9. It is noted that the plurality of cables and hose is preferably routed through the center of the upper robotic arm 810 to the lower robotic arm 812 and end effector 806. Thus, a robotic arm and end actuator may be implemented as using pneumatic bags or a combination, pneumatic bags and cables, or with only cables routed in a way to provide movement that mimics human arm and wrist movement. It is also noted that the pneumatic bags and cables are controlled from a control center that is not depicted in the current figures.

Turning to FIG. 9, a diagrammatic lateral exploded view 900 of the three degrees of freedom radiolucent rotatable, rotational cable actuated robotic arm 802 of FIG. 8 with an end effector 806 utilizing circumduction joint (XYZ turnable hub) 816 is illustrated in accordance with an example implementation of the invention. The upper robotic arm 810 was rotatably coupled to the lower robotic arm 812. The plurality of cables 804 (radiolucent cables) is generally routed through the central axis of the robotic arm 802. The rotation of the lower robotic arm 812 is controlled by cables 814 acting upon lateral rotational windlass 916 via idler pulleys 918. Several axel rods with skate style bearings for guiding cables are depicted in the lower robotic arm 812. The circumduction joint 816 is depicted in this example as being controlled by radiolucent cables 920 for movement in the X/Y axis and up/down of the end effector support 906 and 907. The upper gripper 816 and the lower gripper 818 are coupled together and attached to the end effector support 906 and 907 with pin 820. The upper gripper 816 and lower gripper 818 are biased in a closed position by radiolucent band 822. The pneumatic bag 902 is inflated to open the end effector 806 via hose 904. A hydraulically actuated solenoid manifold 910 controls the gas that inflates/deflates pneumatic bag 902. The nitrogen or hospital air enters a hydraulically actuated solenoid manifold 910 via hose 912 and hydraulic control line 914. In the present implementations, the hydraulically actuated solenoid manifold 910 is made from radiolucent material and controlled by gas. In other implementations, other materials, such as liquid, may be used to inflate and deflate pneumatic bags, such as pneumatic bag 902. Similarly, in non-imaging implementations, the material used in the robotic arm and table may be non-radiolucent.

Figure 10:
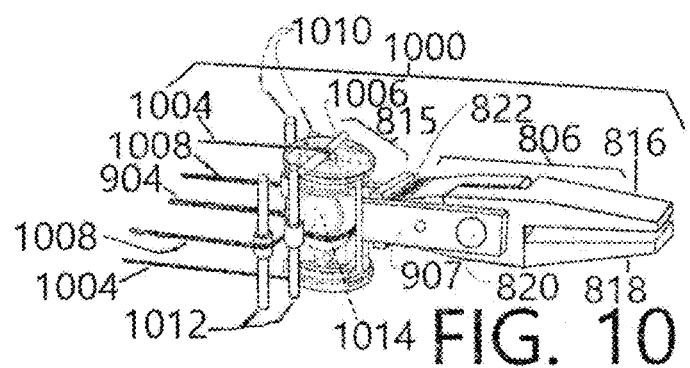
FIG. 10 is an illustration of a radiolucent cable actuated three degrees of freedom circumduction end effector of FIG. 8 in accordance with the example implementation of the invention.

In FIG. 10, an illustration 1000 of a radiolucent cable 1004, 1008 actuated three degrees of freedom circumduction end effector 806 of FIG. 8 is depicted in accordance with the example implementation of the invention. A non-metallic radiolucent cable 1004 is routed through the XYZ turnable hub 816 and moves over the top and bottom axel rods 1006 that are non-metallic radiolucent bearings which spin in the manner of a wheel that enable the non-metallic radiolucent cable 1004 to glide or otherwise move smoothly over the axel rod as the XYZ turnable hub 816 moves the end effector supports 906 of FIGS. 9 and 907 up and down about a central pivot point. It is noted that the axel rod may be implemented as a pin or bolt also and depending upon the implementation may be radiolucent or non-radiolucent. A non-metallic radio lucent cable 1008 is routed through the XYZ turnable hub 816 and across a plurality of non-metallic radiolucent bearings 1010, 1012 for smooth movement of the XYZ turnable hub 816 during horizontal movement of the XYZ turnable hub 816. As described previously, the material used for any of the components in the example implementation may be radiolucent or non-radiolucent depending upon the implementation of the invention.

Figure 11:
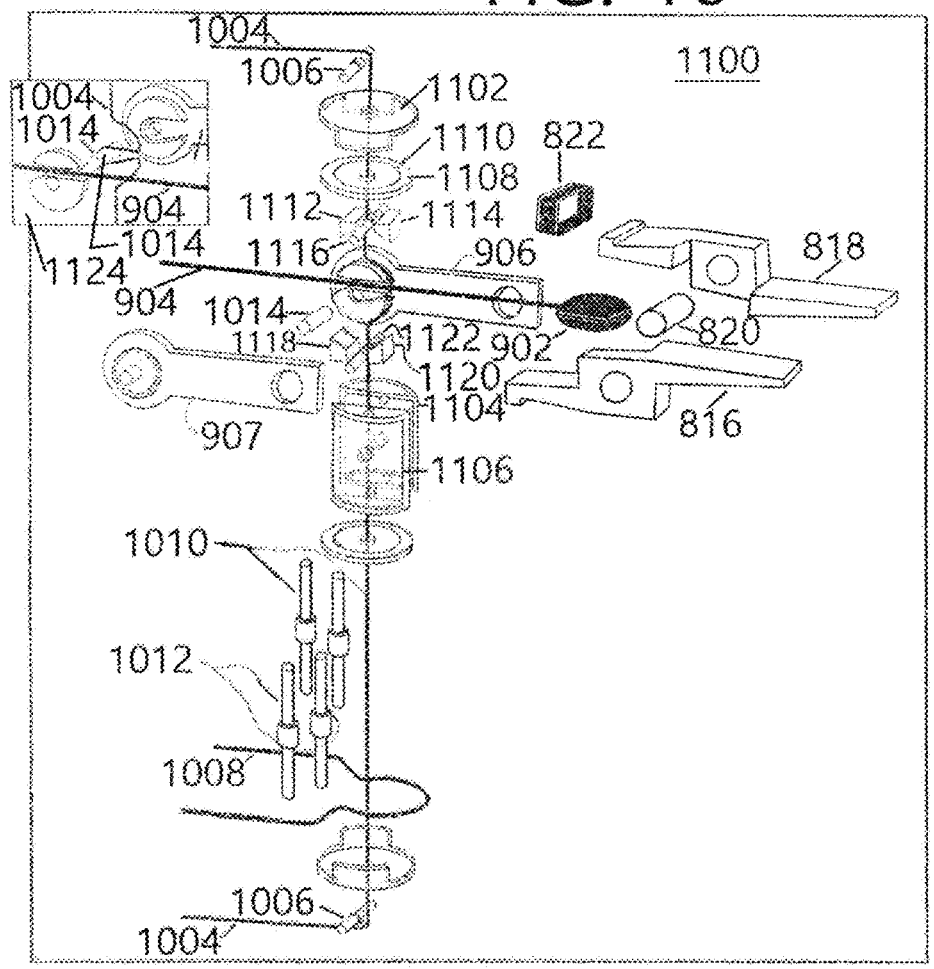
FIG. 11 is an exploded view of the radiolucent cable actuated three degrees of freedom circumduction end effector of FIG. 8 in accordance with the example implementation of the invention.

Turning to FIG. 11 is an exploded view 1100 of the radiolucent cable 1004 and 1008 actuated three degrees of freedom XYZ turnable hub 816 circumduction end effector 806 of FIG. 8 in accordance with the example implementation of the invention. The upper and lower gripper 816 and 818 are pivotally coupled together by pin 820 and biased in a closed position by radiolucent band 822. The radiolucent band 822 is a device that can be stretched when pneumatic bag 902 is inflated and provides a biasing force to return the upper and lower grippers 816 and 818 to their rest position. It is noted that the biasing force is also applying a force on the pneumatic bag 902 that forces deflation when pressure is released via radiolucent hose 904. The grippers 816 and 818 are held in place by end effector supports 906 and 906 that also supports pin 820 and a common axis point at pin 1014.

The up and down motion of the XYZ turnable hub 816 is controlled via cable 1004 and runs across non-metallic radiolucent bearings 1006 through the superior (upper) surface 1102 of the rotational cavity defined by the rotational walls 1104 and 1106 of the XYZ turnable hub 816, equipped with semi-circular guides for horizontal rotation around the central pivot point. The superior surface 1102 covers the superior platform 1108 having a non-metallic radiolucent (in the present implementation) horizontal turntable bearing 1110 that facilitates the smooth turning motion of the XYZ turnable hub 816. Aft 1112 and forward 1114 superior bearing guides for vertical travel of the end effector arms 906 and 907 are depicted with a bearing 1116 for radiolucent cable 1004 to pass between the aft and forward superior bearing guides 1112 and 1114. Similarly, aft 1118 and forward 1120 inferior bearing guides for vertical travel of the end effector arms 906 and 907 are depicted with bearing 1122 for radiolucent cable 1004 to pass between the aft and forward inferior bearing guides 1112 and 1114.

The routing of the non-metallic radiolucent cable 1004 is depicted in the expanded view 1124 as going around part of the end effector arm 906 and pin 1014 is depicted along with the routing path of the hose 904 through a notch along a portion the end effector arm 907. It is noted that an advantage of this routing is a reduction of the flexing of the hose going into the pneumatic bag of the end effector 806. As the hose is maintained in a relatively straight line from the central pivot point (located at the XYZ turnable hub 816) to the pneumatic radiolucent bag 902.

Figure 12:
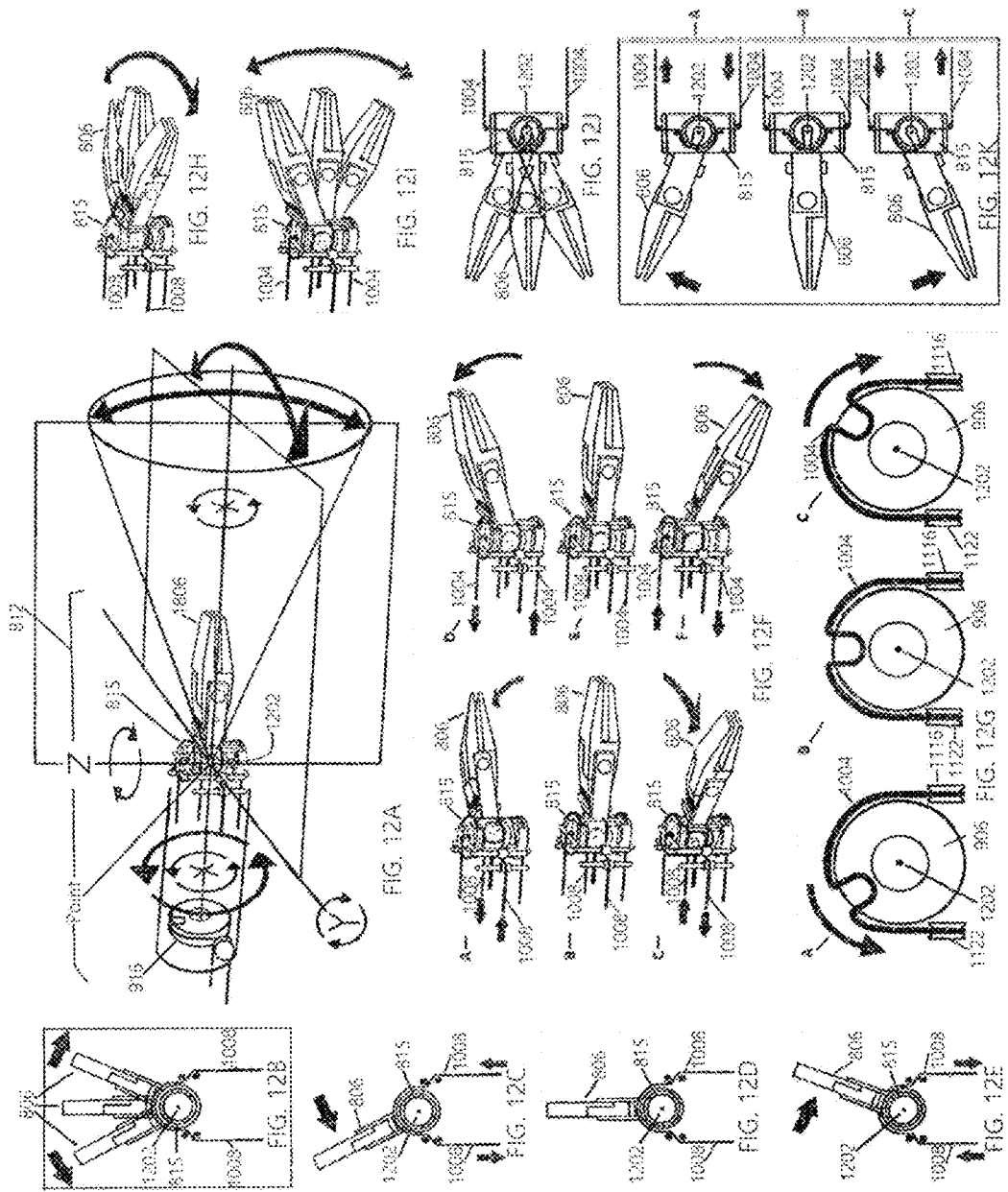
FIGS. 12A-K are diagrams that depict the different positions and movements of the end effector 806 of FIG. 8 in accordance with an example implementation of the invention.

In FIGS. 12A-K, the diagrams depict the different positions and movements of the end effector 806. FIG. 12A illustrates the central rotation point of the three-axis X, Y, and Z of the joint that mimics the human wrist. Of note, in FIGS. 12A-K, is the combination of radiolucent cables 1004 and 1108 working in an example implementation with a radiolucent pneumatic bag 902 of FIG. 9. Thus, in some embodiments, all joints may be moved via pneumatic bags. In other implementations, some joints may be moved by pneumatic bags and cables. In yet other implementations, only cables may be used to implement an XYZ turnable hub with a central axis. It is also noted that all, some or none of the parts that have been described may be implemented with radiolucent materials including laminar sheeting depending upon implementation requirements.

Figure 13:
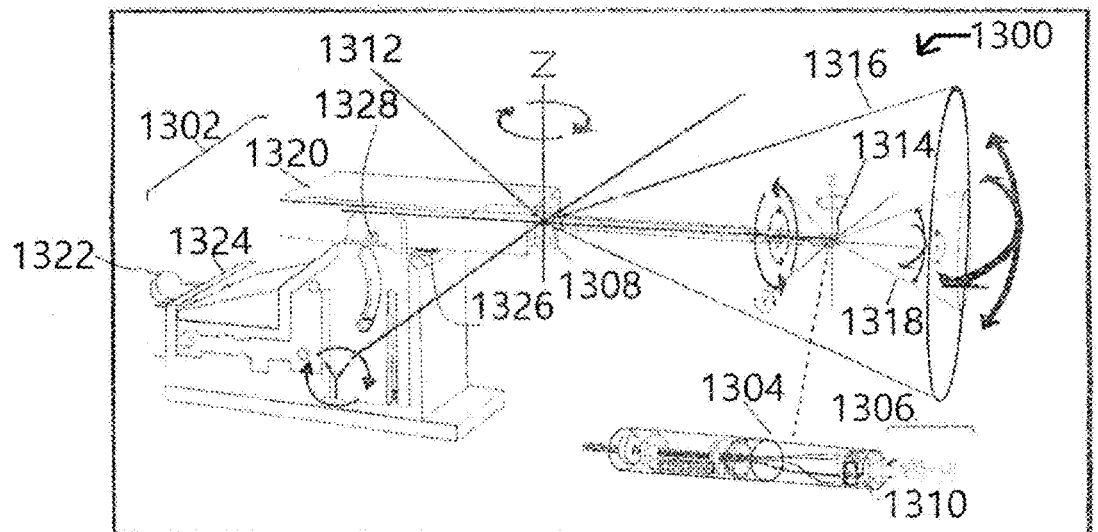
FIG. 13 is a diagram of a radiolucent imaging compatible surgical robotic platform with one radiolucent robotic arm and end effector similar to the robotic arm and end effector depicted in FIG. 4 and also showcases the circumduction cones of movement in accordance with an example implementation of the invention.

Turning to FIG. 13, a diagram 1300 of a radiolucent imaging compatible surgical robotic platform 1302 with one radiolucent robotic arm 1304 and end effector 1306 similar to the robotic arm and end effector depicted in FIG. 4 with the circumduction cones of movement 1316 and 1318 depicted in accordance with an example implementation of the invention. The radiolucent imaging compatible surgical robotic platform 1302 has two radiolucent XYZ turnable hubs 1308 and 1310 with each having a respective pivot point 1312 and 1314. It is also noted that pneumatic bags (one or more) may be employed to lift the robotic arm support structure 1320 along the Z-axis with the gas hoses 1322 that run to the pneumatic bags located in the base 1324 and XYZ turnable hubs 1308 and 1310 along with end effector 1306 pass through base 1324. The robotic arm support structure 1320 is also tiltable by one or more pneumatic bags, such as radiolucent pneumatic bag 1326, at pivot point 1328.

Figure 14:
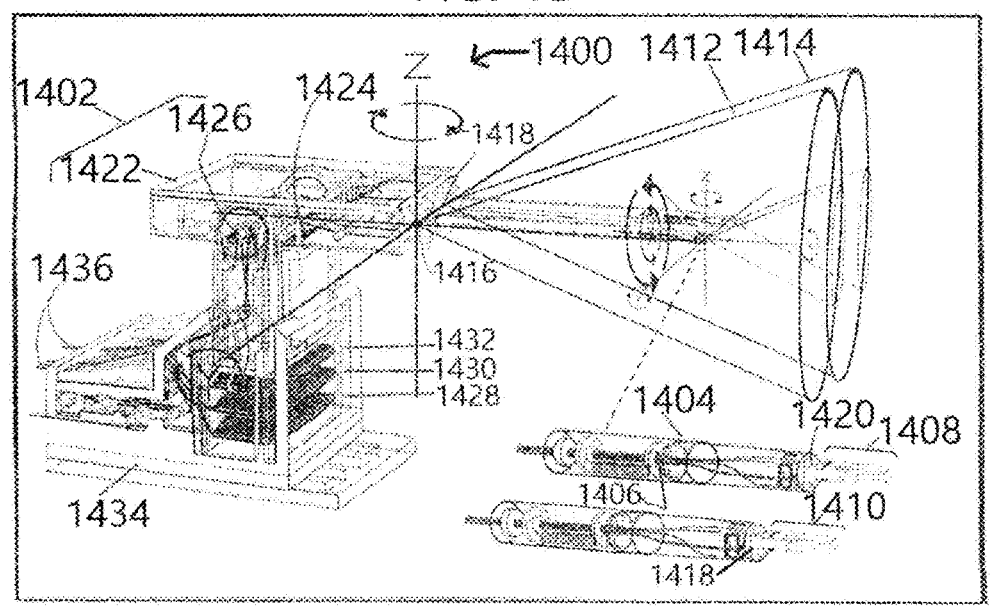
FIG. 14 is a depiction of a radiolucent imaging compatible surgical robotic platform configured with two radiolucent robotic arms and end effectors similar to FIG. 4 with overlapping circumduction cones in accordance with an example implementation of the invention.
Figure 18:
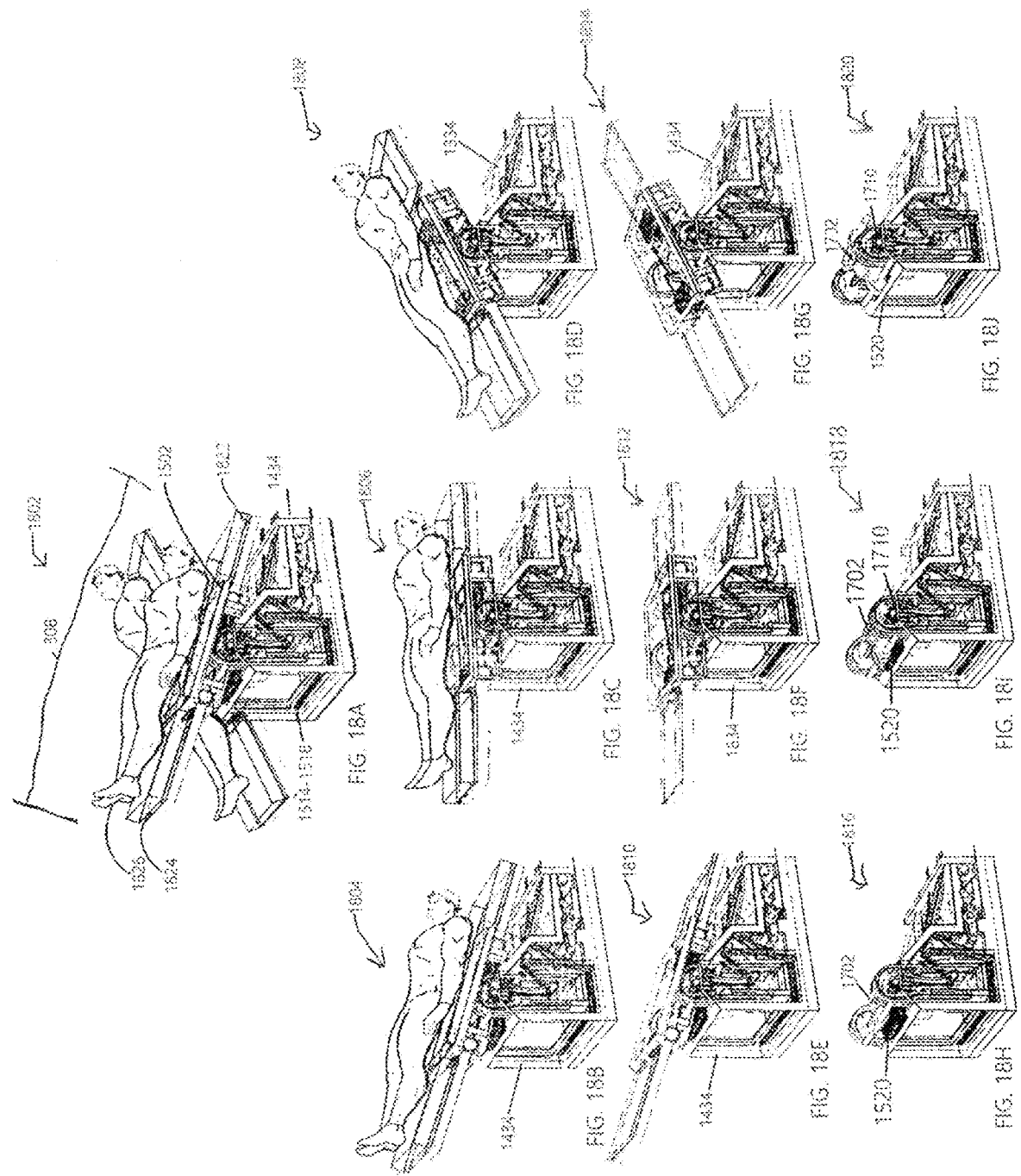
FIG. 18A-18J illustrates the different positions of the radiolucent imaging compatible surgical table of FIG. 3 in accordance with an example implementation.

In FIG. 14, a depiction 1400 of a radiolucent imaging compatible surgical robotic platform 1402 configured with two radiolucent robotic arms 1404 and 1406, each having an end effector 1408 and 1410 similar to FIG. 4 with overlapping circumduction cones 1412 and 1414 in accordance with an example implementation of the invention. Four radiolucent XYZ turnable hubs 1416, 1418, 1440, and 1422 are implemented in the radiolucent imaging compatible surgical robotic platform 1402. Each XYZ turnable hub has a central pivot point as the circumduction cones illustrate. The robotic arm support structure 1422 is tiltable at a pivot point 1426 via a pair of radiolucent pneumatic bags 1424 that control the upward and downward motion of the support structure 1422 and ultimately the four XYZ turnable hubs. Similarly, three radiolucent pneumatic bags 1428, 1430, and 1432 are depicted as being in the base 1434 lifting the robotic arm support structure 1422 along the Z-axis. The base 1434 also is movable along the X-axis via pneumatic bags, cables, or other known methods. A plurality of radiolucent gas hoses 1436 is depicted as entering the base 1434 and are routed to the through the radiolucent imaging compatible surgical robotic platform 1402. In other implementations, a combination of radiolucent cables and radiolucent pneumatic bags may be employed. In yet other implementations only radiolucent cables may be used. It is further understood, that radiolucent parts are used in the example implementation, but in other implementations, a combination of radiolucent parts and non-radiolucent parts may be used. In yet other implementations, only non-radiolucent parts may be used.

Turning to FIG. 15, an illustration 1500 of the radiolucent support structure 1502 and radiolucent base 1434 of FIG. 14 depicting the tilting of the support structure 1502 is shown in accordance with the example implementation of the invention. The support structure 1502 is pivotally coupled 1506 to the base 1434 enabling the tilting of the support structure 1502. Examples of different tilting of the support structure 1502 are depicted in 1508-1512. The tilting of support structure 1502 is with a plurality of radiolucent pneumatic bags 1514-1518 and the tilting of the support structure 1502 is via a pair of radiolucent pneumatic bags 1520. It is noted that the radiolucent base 1434 is shaped with slanted faces 1522 and 1524 that enable increased tilting of the radiolucent support structure 1502. In other implementations, a combination of pneumatic bags and cables may be used. In yet other implementations, non-radiolucent pneumatic bags may be used depending upon the implementation requirements.

In FIG. 16, an illustration of the radiolucent cable braking mechanism of FIG. 15 is depicted in accordance with and example implementations. When the radiolucent support structure 1502 is in position 1512 for FIG. 15, the radiolucent cables 1602 are shown routed in a manner to enable them to travel freely as the table is tilted in FIG. 15. When the radiolucent support structure 1502 is in position 1510 for FIG. 15, the radiolucent cables 1602 are shown routed in a manner to avoid disruption and prevent shacking or shimmying the table of FIG. 15. When the radiolucent support structure 1502 is in position 1508 for FIG. 15, the radiolucent cables 1602 are shown routed in a manner to avoid movement of the table of FIG. 15.

Turning to FIG. 17, an illustration of the tilting of the radiolucent support structure 1502 of FIG. 15 is accomplished with a pair of radiolucent pneumatic bags 1520 and 1710 is depicted in accordance with an example implementation of the invention. When the radiolucent support structure 1502 is in position 1508 the radiolucent base 1434 supports a radiolucent dual rhombus bilateral effort arm of the actuation of Trendelenburg tilt member 1702 that has a forward vertical rotation load-lifting rod 1706 and aft vertical rotation load-lifting rod 1704. The radiolucent dual rhombus bilateral effort arm of the actuation of Trendelenburg tilt member 1702 is depicted as being privately supported by an inflation platform 1708 that raised and lowered via pneumatic bags 1514-1518.

The radiolucent pneumatic bag 1520 is inflated and presses upon one side of the radiolucent dual rhombus bilateral effort arm of the actuation of Trendelenburg tilt member 1702 while deflating radiolucent pneumatic bag 1710 resulting in the radiolucent support structure 1502 moving to position 1508. When the radiolucent pneumatic bags 1520 and 1710 are inflated with approximate equal pressure, the radiolucent support structure 1502 moves to position 1510. When the radiolucent pneumatic bag 1710 is inflated and presses upon one side of the radiolucent dual rhombus bilateral effort arm of the actuation of Trendelenburg tilt member 1702 and radiolucent pneumatic bag 1520 is deflated, the radiolucent support structure 1502 moves to position 1512

In FIG. 18A-J, illustrations 1802-1820 of the different positions of the radiolucent imaging compatible surgical table 308 of FIG. 3 in accordance with an example implementation. The radiolucent imaging compatible surgical table 308 has the radiolucent support structure 1502 with a forward and aft extension 1822 and 1824. Together 1502, 1822, and 1824 form a support surface to support the object being imaged, in this case, a person 1826. The FIGS. 18A-J, illustrate the surgical table 308 being tilted in different directions (up and down) and the radiolucent pneumatic bags 1520 and 1710 that cause the radiolucent dual rhombus bilateral effort arm of the actuation of Trendelenburg tilt member 1702 to tilt. It is noted that radiolucent pneumatic bags 1514-1518 are depicted as being deflated and the radiolucent support structure 1502 is in its lowest position.

Figure 19:
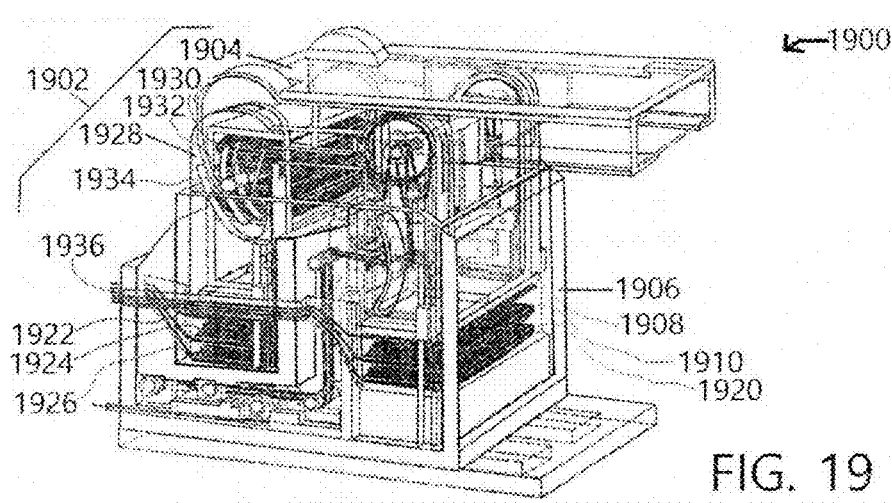
FIG. 19 illustrates a height-adjustable, articulating, actuating, Trendelenburg, and reverse Trendelenburg radiolucent bariatric imaging compatible surgical table structure that includes a radiolucent one piece table top housing and base in accordance with an example implementation.

Turning to FIG. 19, a diagram 1900 of a height-adjustable, articulating, actuating, Trendelenburg, and reverse Trendelenburg radiolucent bariatric imaging compatible surgical table structure 1902 that includes a radiolucent one piece table top housing 1904 and base 1906 is illustrated in accordance with an example implementation. It is understood that a bariatric table in general needs to support a patient who is above average weight and thus needs to be able to move and orient the patient while on the surgical table. Thus, the base 1906 has a radiolucent dual pylon member 1928 with each pylon supported by a plurality of radiolucent pneumatic bag stacks 1908-1920 and 1922-1926. The two groups of radiolucent pneumatic bags work in unison to change the height of the radiolucent one piece table top housing 1904. The tilting of the radiolucent one piece table top housing 1904 is controlled by a plurality of stacked radiolucent pneumatic bags 1930-1932 located on one end of the radiolucent one piece table top housing 1904 and not at the pivot point of the radiolucent one piece table top housing 1904. The hoses 1936 for the radiolucent pneumatic bags 1908-1922 and 1930-1934 are routed out of the rear of the base 1906.

Figure 20A:
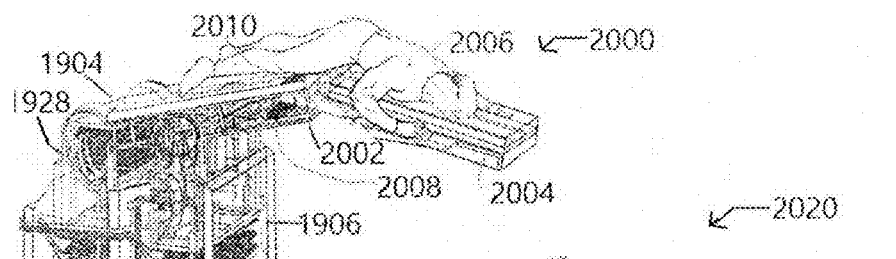
FIG. 20A-C illustrates the height-adjustable, articulating, actuating, Trendelenburg, and reverse Trendelenburg radiolucent bariatric imaging compatible surgical table structure of FIG. 19 with attachments in accordance with an example implementation of the invention.
Figure 20B:
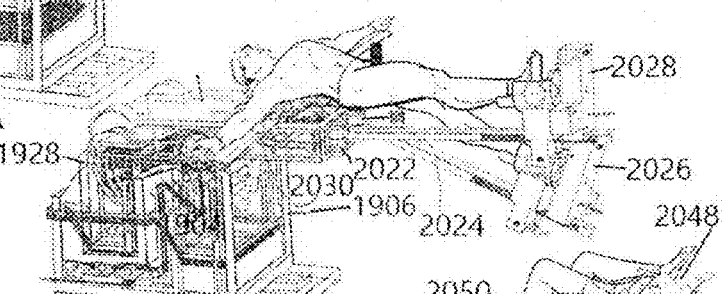
Figure 20C:
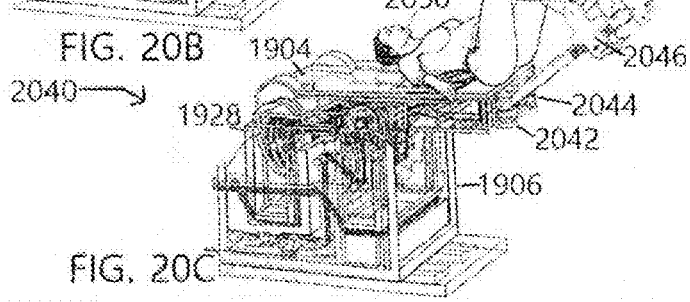

In FIGS. 20A-C, illustrations 2000, 2020, and 2040 of height-adjustable, articulating, actuating, Trendelenburg, and reverse Trendelenburg radiolucent bariatric imaging compatible surgical table structure (radiolucent surgical table structure) 1904 of FIG. 19 with different radiolucent attachments 2004, 2224, 2226, 2046 and 2048 are depicted in accordance with an example implementation of the invention. The attachments generally are coupled to the end of the surgical table structure 1904 on the side opposite the dual pylon member 1928. It is noted that in 20A, a pair of radiolucent pneumatic bags 2008 and 2010 act on opposite sides of a rhomboidal shaped member coupled to table attachment 2004 and control the tilt of the radiolucent table attachment 2004 relative to the surgical table structure 1904. The surgical table structure 1904 is supported by the base 1906 and moved up or down via the dual pylon member 1928 is supported by a plurality of radiolucent pneumatic bags. The tilt of the radiolucent table attachment 2004 relative to the radiolucent surgical table structure 1904 enables a patient 2006 to be positioned in various lumbar flexion position.

The attachments 2024 and 2026 of FIG. 20B are coupled to the radiolucent surgical support table 1904 at XYZ turnable hubs 2022 and 2024 that each enable movement and control of a radiolucent foot positioner 2026 and 2028, respectively. FIG. 20B depicts the XYZ turntable hub being utilized for either hip or lower extremity surgery. Similarly, radiolucent pneumatic joints are used to control arm supports 2030 (another radiolucent pneumatic joint is not visible under the patient in FIG. 20B). It is noted that the joints may be radiolucent pneumatic joints, radiolucent cable joints, or a combination of radiolucent pneumatic joints and radiolucent cable joints depending upon the implementation requirements (i.e. imaging, imaging and surgical, just surgical, non-medical). Similarly, the need for the radiolucent properties of the structures and joints is dependent upon the implementation requirements.

The attachments 2046 and 2048 of FIG. 20C are coupled to lithotomy hubs 2042 and 2046 are used to place the patient 2050 in the lithotomy position that is commonly used to access the pelvis and perineum during urological, colorectal, and gynecological surgery as well as during the birthing process. The respective lithotomy hub 2042 or 2044 is a radiolucent joint with a bilateral slotted rack for locking the respective foot positioner 2046 and/or 2048 in the desired position. The movement of the lithotomy hub is by radiolucent pneumatic bag pairs acting upon a rhomboidal member within the hub 2042 or 2044.

Turning to FIG. 21, an illustration 2100 of the radiolucent dual pylon member 1928 of FIG. 19 is depicted in accordance with an example implementation of the invention. The radiolucent dual pylon member 1928 has two pylons 2102 and 2104 that support the one-piece tabletop housing 1904 at pivot point 2106 and with radiolucent bags 1930-1935. A radiolucent load-lifting pole with bearings 2108 moves within slots, such as slot 2110 and is placed between or beneath the radiolucent pneumatic bags 1930-1935. Depending upon the placement of the radiolucent load-lifting pole with bearing 2108 and the inflation of the radiolucent pneumatic bags 1930-1935, different angles of tilt 2110-2114 up or down of the one-piece tabletop housing 1904 is achieved.

In FIG. 22A-C, illustrations of the radiolucent cable breaking mechanism of surgical table of FIG. 19 for in accordance with an example implementation of the invention. In FIG. 22A, the one-piece tabletop housing 1904 can tilt to position 2114 of FIG. 21 and the radiolucent cables 2202 are not bound or pinched when the surgical table is tilted. The routing of the radiolucent cables 2202 also enables the radiolucent dual pylon member 1928 to be raised and lowered without binding or pinching the radiolucent cables 2202. Similarly, in FIG. 22B, the one-piece tabletop housing 1904 can tilt to position 2112 of FIG. 21 and the radiolucent cables 2202 are not bound or pinched. In FIG. 22C, the one-piece tabletop housing 1904 can tilt to position 2110 of FIG. 21 and the radiolucent cables 2202 are not bound or pinched. It is noted that the radiolucent cable breaking mechanism prevents movement or shimmying of the surgical table.

Turning to FIGS. 23A-C, illustrations the position of the radiolucent load-lifting pole of FIG. 21 with bearings 2108 and its effect on the positioning of the one-piece tabletop housing 1904 in accordance with an example implementation of the invention. The radiolucent dual pylon member 1928 has a slot 2302 that the radiolucent load-lifting pole with bearing 2108 extends through. The one-piece tabletop housing 1904 is coupled to the radiolucent load-lifting pole with bearing 2108. The radiolucent load-lifting pole 2108 moves and lifts the one-piece tabletop housing 1904. In FIG. 23B, the radiolucent pneumatic bags 1930-1935 are place between the radiolucent pneumatic bags at a different location to achieve different amounts of lift that result in a different amount of tilt 2110, 2112, and 2114. In general, the current embodiment demonstrates the more radiolucent pneumatic bags 1930, 1934, and 1935 below the radiolucent load-lifting pole with bearing 2108 the more tilt occurs as demonstrated in FIG. 23C. The plurality of radiolucent pneumatic bags 1930-1935 may have some of them being filed while others emptied to more smoothly and concisely tilt. In other implementations, the one-piece tabletop housing 1904 may be biased in a direction (either tilted up or down) and radiolucent pneumatic bags may act against the bias force resulting in tilting of the one-piece tabletop housing 1904.

Figure 24:
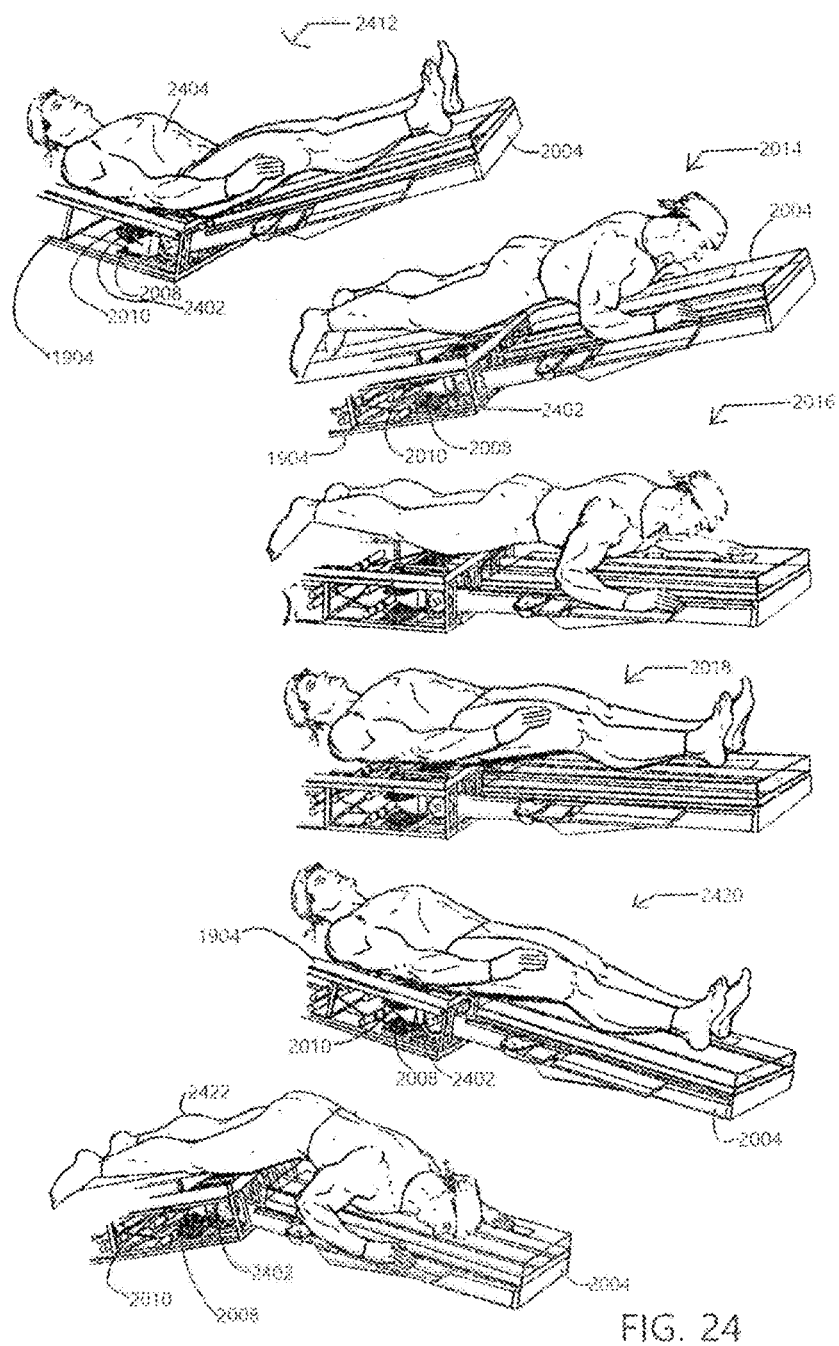
FIG. 24 illustrates the different positions that may be achieved using the radiolucent one piece table top housing with table attachment in accordance with an example implementation of the invention.

In FIG. 24, an illustration of the different positions that may be achieved using the radiolucent one piece table top housing 1904 with table attachment 2004 is depicted in accordance with an example implementation of the invention. Rhomboidal shaped member 2402 is acted on a pair of radiolucent pneumatic bags 2008 and 2010 to tilt upward placing the patient 2404 in a "v" type position 2412 with both head and legs raised. A patient may be inclined upward 2414 on a flat surface by having the one-piece tabletop housing 1904 level along with table attachment 2004. Similarly, the patient may be supported in a horizontal position 2416 It is noted that a patient may be face up or face down with their head on the pneumatic bag side or table attachment 2004 side as illustrated in 2416 and 2418. A patient may also be declined downward 2020 on a declined surface by having the one-piece tabletop housing 1904 with the table attachment 2004 angle straight out from the one-piece tabletop housing 1904. The patent 2422 may be placed into an inverted 'v' with the one-piece tabletop housing 1904 tilted up and the table attachment 2004 tilted down. The rhomboidal shaped member 2402 is acted upon by a pair of radiolucent pneumatic bags 2008 and 2010 to tilt the table attachment 2004 in a downward angle.

Figure 25:
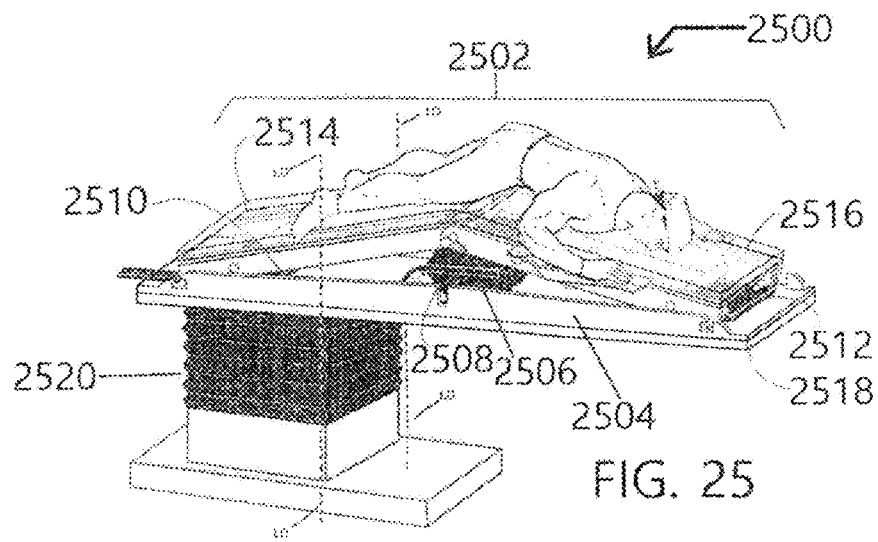
FIG. 25 illustrates a radiolucent imaging compatible flexion/extension spine table retro-fit top, utilizing one degree of freedom radiolucent flexion/extension hinge in accordance with an example implementation of the invention.

Turning to FIG. 25, a depiction 2500 of a radiolucent imaging compatible flexion/extension spine table 2502 retro-fit top 2504, and utilizing one degree of freedom radiolucent flexion/extension hinge 2506 is illustrated in accordance with an example implementation of the invention. The retrofit top 2504 is depicted with a plurality of radiolucent pneumatic bags 2508, 2510, and 2512. The radiolucent pneumatic bags 2508-2512 may be inflated and deflated independently to rise and lower associated surfaces of the retro-fit top 2514 and 2516 that are coupled together at radiolucent flexion/extension hinge 2506 enabling one degree of movement. The retro-fit top 2504 is affixed to the original surgical tabletop 2518 that can be raised and lower via its base 2520.

Figure 26:
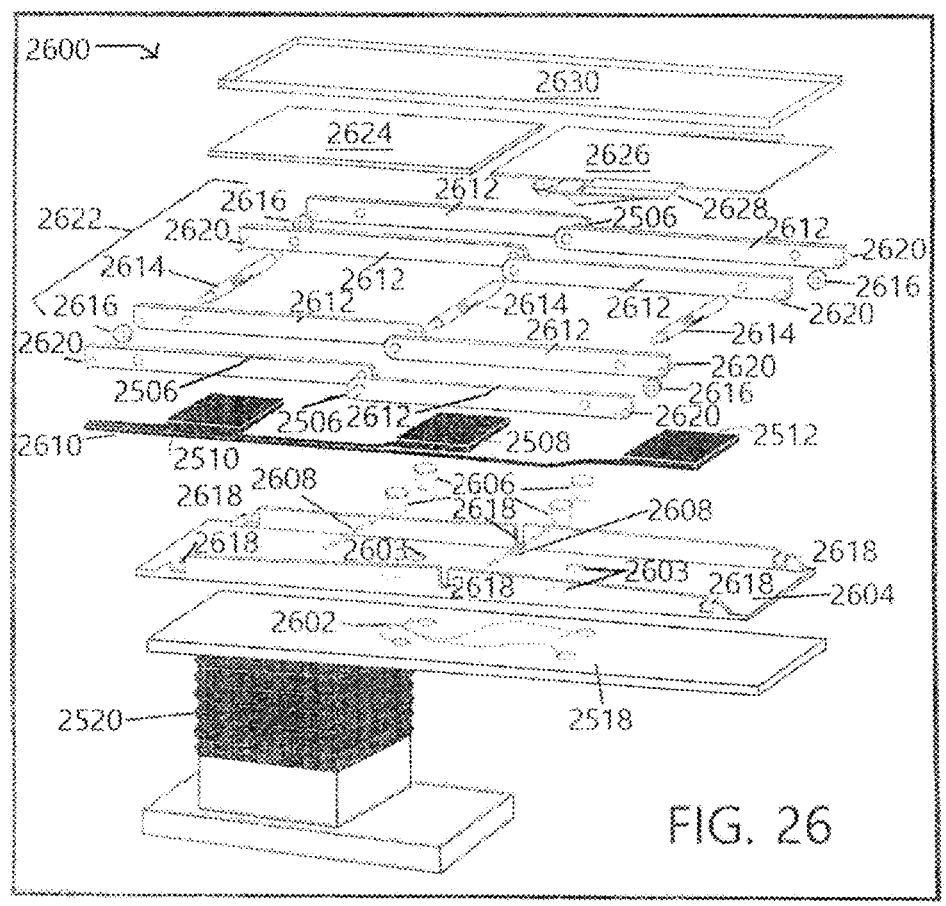
FIG. 26 illustrates the parts of the radiolucent imaging compatible flexion/extension spine table retro-fit top of FIG. 25 in accordance with an example implementation of the invention.

In FIG. 26, an illustration 2600 of the parts of the radiolucent imaging compatible flexion/extension spine table retro-fit top 2502 of FIG. 25 in accordance with an example implementation of the invention. The base 2520 supports the original surgical tabletop 2518 has a plurality of holes or fenestrations 2602. The holes 2602 align with holes 2603 in the tray 2604 and radiolucent attachment plugs 2606 are inserted through the holes and locked into place with radiolucent cotter pins 2608. The radiolucent cotter pins may be made from DELRYN, PEEK, or other strong radiolucent material. Radiolucent pneumatic bags 2508-2512 and their associated hoses 1610 are used to flex the radiolucent flexion/extension hinge 2506 that is made up of radiolucent supports members 2612 coupled together by radiolucent lift poles 2614 and radiolucent roller bearing 2616 for translation of planar/laminar arms 2612 during central apex vertical elevation and descent of radiolucent hinge 2506. The radiolucent support members 2612 have rolling guide pins 2620 for securing the radiolucent hinge 2506 that rest in slots 2618. The end slots also enable slight movement of the rolling guide pins 2620 that secure the rolling guide pins 2620 from slipping out of the slots 2618.

The support structure 2622 supports to radiolucent sheet tabletops 2624 and 2626 that are affixed to each side of the radiolucent hinge 2506. The affixing of the radiolucent sheet tabletops 2624 and 2626 may be with radiolucent fasteners (screws, nails, dowels) and/or radiolucent adhesive. Radiolucent sheet 2626 may optionally have a radiolucent upper extremity positioner 2628 (typically one on each side) that supports a patient's arms. A radiolucent table pad 2630 then covers the radiolucent sheet tabletops 2624 and 2626.

Turning to FIG. 27A-C, illustrations of the radiolucent imaging compatible flexion/extension spine table retro-fit top 2502, utilizing one degree of freedom radiolucent flexion/extension hinge 2506 of FIGS. 25 and 26 with a patient 2702 in different positions is depicted in accordance with an example implementation. The base 2520 can rise and lower the radiolucent imaging compatible flexion/extension spine table retro-fit top 2502. In FIG. 27A, the patient 2702 is flat on the radiolucent imaging compatible flexion/extension spine table retro-fit top 2502. In FIG. 27B, the patient 2702 is flexed in the middle with the middle of the radiolucent imaging compatible flexion/extension spine table retro-fit top 2502 being raised by radiolucent pneumatic bag 2508. In FIG. 27C, the patient 2702 is flexed with the head and feet of the patient being raised by the radiolucent imaging compatible flexion/extension spine table retro-fit top 2502 by radiolucent pneumatic bags 2510 and 2512.

In FIGS. 28A-C, illustrations of the radiolucent imaging compatible flexion/extension spine table retro-fit top 2502, utilizing one degree of freedom radiolucent flexion/extension hinge 2506 of FIGS. 25, 26, and 27A-27C with imaging devices 2802, 2804, and 2806 and the computer assisted guidance system 2808 is depicted in accordance with an example implementation of the invention. The base 2502 enables a patient to raise or lower to generally be placed in the imaging area and the radiolucent pneumatic bags 2508-2512 enable the orientation of the patient on the radiolucent imaging compatible flexion/extension spine table retro-fit top 2502. Optical/laser tracking arrays 2810 and 2812 for identifying the location and assist in the movement of the radiolucent imaging compatible flexion/extension spine table retro-fit top 2502. The optical/laser tracking arrays 2810 and 2812 may also use LiDAR or other known distance motion-sensing approaches. The radiolucent imaging compatible flexion/extension spine table retro-fit top 2502 may have target points placed upon its frame that enable the optical tracking arrays 2810 and 2812 to identify locations and movements of the target points. The data gathered by the optical/laser tracking arrays 2810 and 2812 is transmitted to the computer assisted guidance system 2808.

Turning to FIG. 29, an illustration 2900 of a pneumatically actuated radiolucent skull clamp 2902 utilizing rotatable radiolucent hinge joints 2904 and 2906 comprised of laminar sheeting that enable greater surgeon control of verifiable clamp force to the skull 2914 that is part of a surgical table 2916 similar in operation to the surgical table of FIG. 3 and clamp hand controller 2916 in accordance with an example implementation of the invention. A patient's head/skull 2914 is positioned between the clamp arms 2908 and 2909 of the pneumatically actuated radiolucent skull clamp 2902 and held by skull pins 2910 and 2912. The clamp arms are pivotally connected 2906 and biased in a closed position by a radiolucent flexible band 2920. A radiolucent pneumatic bag 2924 is inflated using hand controller 2916 with gas hose 2918 to inflate the radiolucent pneumatic bag 2924 to an open position with the fully open position achieved by completely squeezing 2926 the hand controller 2916. The amount of pressure asserted by the skull pins 2910 and 2912 is very precisely controlled. In other implementations, pressure sensors may couple to the pneumatically actuated radiolucent skull clamp 2902. An advantage of using the radiolucent pneumatic bag 2922 for asserting force on the skull clamp 2902 is pressure sensors may be placed on, in, or next to the radiolucent bag to measure the pressure that is being asserted on the skull 2914 at a location away from the skull 2914. In yet other implementations, the pressure measurement may be made at the hand controller or some other location along with the gas hose 2918 that is not in the image area around the skull 2914. The pneumatically actuated radiolucent skull clamp 2902 may also have cable control 2924 control the general position of the pneumatically actuated radiolucent skull clamp 2902.

In FIG. 30, the operation of the radiolucent skull clamp 2902 of FIG. 29 is depicted in accordance with the example implementation of the invention. The skull 2914 of a patient is immobilized by the radiolucent skull claim 2902. The clamp arms 2908 and 2909 are biased in a closed position by the radiolucent band 2920 (Flexor Tension Band). The ends of the claim arms 2908 and 2909 have skull pins 2910 and 2912 that press on the skull 2914 to immobile the skull 2914. The inflation of the radiolucent pneumatic bag 2922 causes the clamp arms 2910 and 2912 to reduce pressure and ultimately fully open if fully inflated.

Turning to FIG. 31, the joint 2906, 3116, and 3118 of clamp arms made from laminar sheets that make up the radiolucent skull clamp 2902 is depicted in accordance with the example implementation of the invention. The radiolucent skull clamp 2902 may be made up of multiple sheets of radiolucent laminar sheets that are pivotally coupled at a joint 2906, 3116, and 3118 with each joint coupling together a different number of laminar sheeting. The radiolucent skull clamp 2902 is depicted with a different number of laminar sheeting making up the claim arms that terminate in skull pins 2910 and 2912. A pneumatic bag 2922 and radiolucent band 2920 act on the radiolucent sheeting in the same manner, regardless of the number of layers of sheeting. The radiolucent joint 2906, 3116 and 3118 is created by the laminar sheets being coupled together by a radiolucent pin 3108 as shown in 3102, 3104, and 3106. In other implementations, other types of radiolucent fasteners, such as screws, nuts, and bolts, rivets may be employed. The radiolucent pin 3108 will have length dictated by the number of laminar sheeting as the more laminar sheets used, the longer the radiolucent pin 3108 will be. The radiolucent pin 3108 may be an assembly of a radiolucent head 3110, radiolucent body 3112, and a radiolucent cotter pin 3114 that prevents the radiolucent pin 3108 from falling out. The assembled radiolucent pin 3108 has a hole 3114 defined by the radiolucent body 3112 through the radiolucent body 3112 for the radiolucent cotter pin 3114 to pass through and secure the clamp arms.

In FIG. 32A, an illustration 3200 of the radiolucent surgical table 318 of FIG. 3 with radiolucent table attachment 3202 in an operating room with the optical tracking arrays 2810 and 2812 and the computer assisted guidance system 2808 of FIG. 28 is depicted in accordance with an example implementation of the invention. A patient may be rested upon the radiolucent surgical table 318 with radiolucent table attachment 3202 and moved into an imager, such as "O" ring 304 to have surgery using a surgical robot 306 of FIG. 3. The radiolucent pneumatic bags that control the radiolucent surgical table 318 and radiolucent bags 3204 that control the up and down motion of the table attachment 3202 receive pressurized gas, such as nitrogen or oxygen, via gas hoses 3203 that are retractable and stored on hose reel 3205. The gas hoses 3203 are pulled out of and retracted into the hose reel 3205 in response to movement of the radiolucent surgical table 318. It is noted that a generally shaped radiolucent rhomboidal member is part of the radiolucent joint 3206 for tilting the table attachment 3202 up and down. The gas hoses 3203 are coupled to a hydraulic micro-solenoid manifold 3207 that is made from radiolucent non-metallic material. Similarly, the lines 3209 that run to the radiolucent pneumatic bags are coupled to the hydraulic micro-solenoid manifold 3207.

The movement of the radiolucent surgical table 318 and table attachment 3202 is controlled from the computer assisted guidance system 2808. The position of the radiolucent surgical table 318 and table attachment 3202 is displayed on screen 3212. The screen 3212 may be a touch screen that allows a person 3212 to simply move the joints on the screen with the computer assisted guidance system translating the new position on the screen to commands and issue the commands to inflate and deflate the different radiolucent pneumatic bags (and/or cables) that control the position of the radiolucent surgical table 318 and table attachment 3202. The optical tracking arrays 2810 and 2812 track the position of the radiolucent surgical table 318 and table attachment 3202 by using optical image processing, such as tracking targets placed upon the radiolucent surgical table 318 and table attachment 3202. In other implementations location sensors in the joints may be used, LiDAR or similar technologies may be employed. FIG. 32B illustrates some of the positions the radiolucent surgical table 318 and table attachment 3202 using the radiolucent joint 3206 for tilting the table attachment 3202 and radiolucent bags 3204 up and down.

The radiolucent surgical robot 306 may be controlled by a gestural podium 3220 depicted in FIG. 32C has optical tracking arrays 3222 and 3224 for tracking hand movements of a surgeon 3218. The hand of the surgeon 3218 are depicted with fiducial marker equipped gloves 3228 and 3230. A processor or controller and associated memory and programming, such as found in a computer or Arduino microcontroller, computer, cellular tablet, and cellular telephone executes software to identify the motions of the fiducial markers into instructions for the radiolucent solenoid manifold. In other implementations, other types of hand movement tracking may be used, such as LiDAR, acoustic distancing devices, optical image processing without fiducials, to give but a few examples. The radiolucent end effectors of the robot arms are captured by a video imaging device and displayed upon display 3226 of the gestural podium 3220. It is also noted that gestures may be used to switch screens and operation of devices, such as switching between the surgical robot and surgical table.

The movement of the surgeon's hands are mimicked by the surgical robot 306 with the use of the Radiolucent Robotic XYZ three degrees of circumduction enabled end effectors of the robot arms that can articulate in the same manner as the surgeon's hands wearing the fiducial marker equipped gloves 3228 and 3230, as the human wrist is itself a circumduction enabled joint with the ability to perform both rotation and circumduction originating from the radius bone of the human wrist as the one common pivot point of the wrist X, Y and Z axes. Thus it is the distal tip of the radius bone in the wrist which is equivalent to the one fixed central pivot point with all flexion extension, abduction adduction functions of the wrist describing a circumduction cone as previously described, just as radiolucent robotic circumduction and Rotation Enabled three degree of freedom end effectors are enabled to perform this circumduction function within circumduction cone with the apex of said cone originating at the one central pivot point within the radiolucent XYZ Hub.

It is also noted that gas pressure sensors measure the amount of gas pressure at each of the radiolucent pneumatic bags. If a bag or hose fails and the minimum pressure is not maintained, a signal is generated in response to the sensor and displayed on display 3226 or 3212. Furthermore, an alarm may also sound to signal a radiolucent bag failure. In the current implementations, the gas pressure sensors are located in the radiolucent pneumatic bags are coupled to the hydraulic micro-solenoid manifold 3207. The signaling between the pressure sensors and the gestural podium 3220 may be wired or wireless, such as Bluetooth.

The radiolucent pneumatic bags may be constructed to be duel chambered with an independent hose used to inflate each chamber. If a failure occurs and is detected by a pressure sensor, an alarm will be issued. But, the surgery may continue as the redundant radiolucent chamber will enable the safe operation of the surgical robot.

Figure 32:
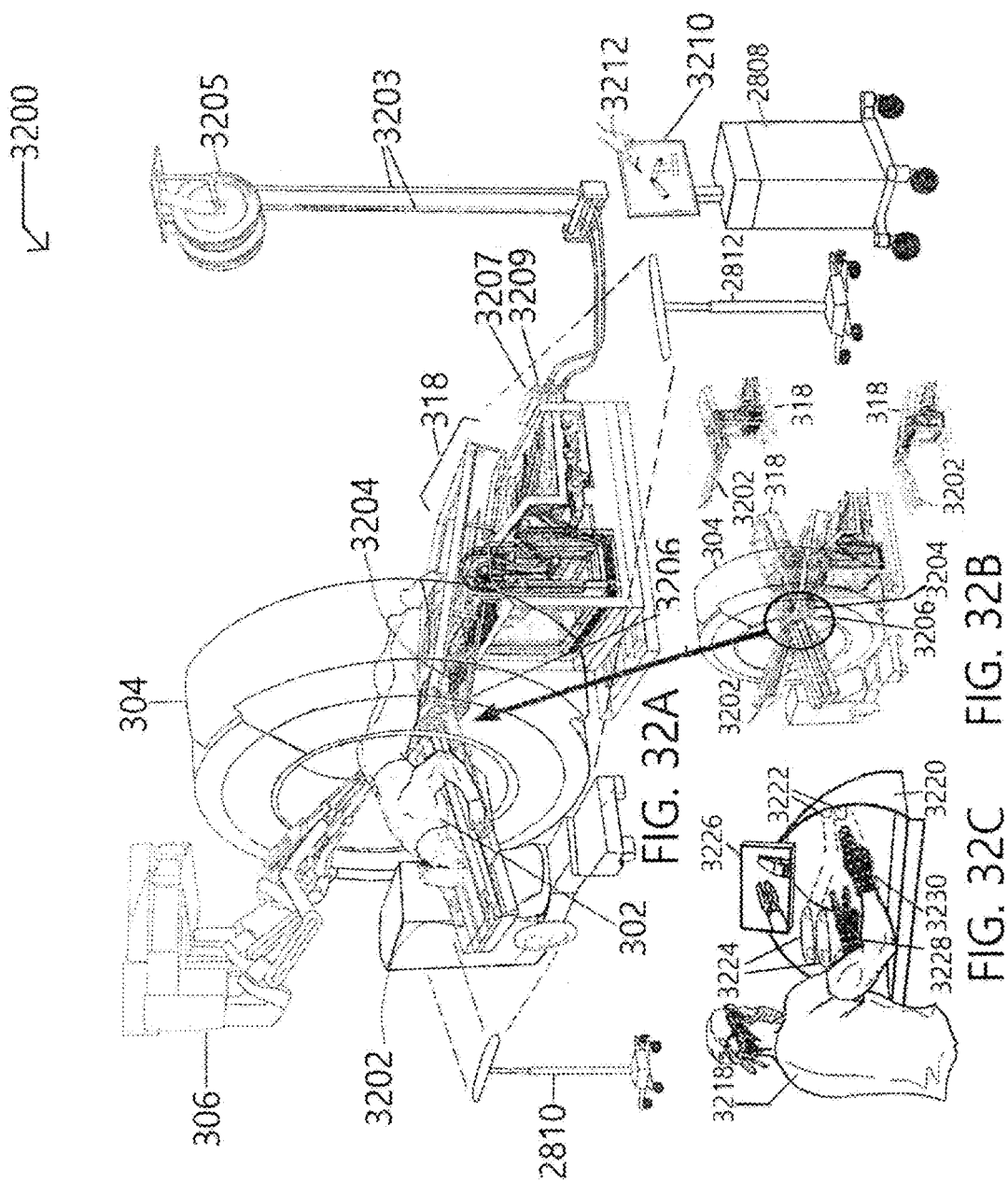
FIGS. 32A-C illustrate the radiolucent surgical table of FIG. 3 with radiolucent table attachment in an operating room with the optical tracking arrays and computer-assisted guidance system of FIG. 28 in accordance with an example implementation of the invention.
Figure 33:
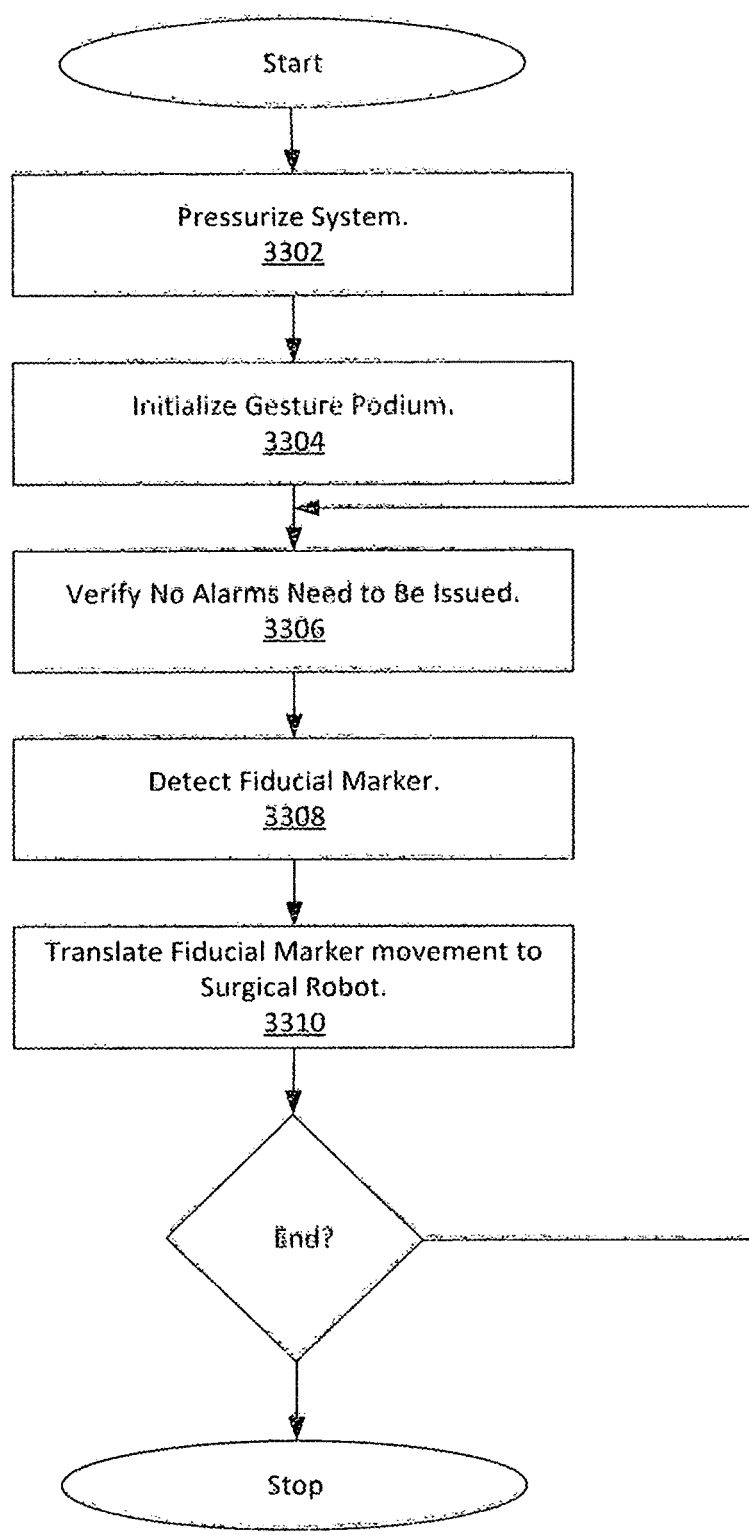
FIG. 33 is an illustration of a flow diagram of the use of radiolucent pneumatic bags controlled by the computer assisted guidance system of FIG. 32 in accordance with an example implementation of the invention.

Turning to FIG. 33 is an illustration of a flow diagram 3300 of the use of radiolucent pneumatic bags controlled by the computer-assisted guidance system of FIG. 32 in accordance with an example implementation of the invention. The radiolucent robotic surgical robot and radiolucent surgical table that use radiolucent pneumatic bags have their systems pressurized 3302. The control system, gesture podium, is initialized 3304. A self-check of the pressurized system occurs and alarms issued if faults are detected in 3306. The surgeon places his hands in fiducial marked gloves and places them in the optical monitoring part of the controller and the control system then identifies the location of the fiducial markers 3308. The movement of the fiducial markers are then tracked and translated to the movement of the surgical robot 3310. If the operation is over, then the gesture podium may be turned off and surgery is complete, otherwise, a check for errors continues to occur 3306 and the fiducial marks are continued to be used to translate motion from the surgeon's hands to the surgical robot 3308 and 3310.

It will be understood and is appreciated by persons skilled in the art, that one or more processes, sub-processes, or process steps described in connection with FIG. 33 may be performed by hardware and/or software (machine-readable instructions). If the approach is performed by software, the software may reside in software memory in a suitable electronic processing component or system such as one or more of the functional components or modules schematically depicted in the figures.

The software in software memory may include an ordered listing of executable instructions for implementing logical functions (that is, "logic" that may be implemented either in digital form such as digital circuitry or source code or in an analog form such as analog circuitry or an analog source such an analog electrical, sound or video signal), and may selectively be embodied in any computer-readable medium for use by or in connection with an instruction execution system, apparatus, or devices, such as a computer-based system, processor containing system, or other systems that may selectively fetch the instructions from the instruction execution system, apparatus, or device and execute the instructions. In the context of this disclosure, a "computer-readable medium" is any tangible means that may contain or store the program for use by or in connection with the instruction execution system, apparatus, or device. The tangible computer-readable medium may selectively be, for example, but is not limited to, an electronic, magnetic, optical, electromagnetic, or semiconductor system, apparatus or device. More specific examples, but a non-exhaustive list, of tangible computer-readable media, would include the following: a portable computer diskette (magnetic), a RAM (electronic), a read-only memory "ROM" (electronic), an erasable programmable read-only memory (EPROM or Flash memory) (electronic) and a portable compact disc read-only memory "CDROM" (optical). Note that the tangible computer-readable medium may even be paper (punch cards or punch tape) or another suitable medium upon which the instructions may be electronically captured, then compiled, interpreted or otherwise processed in a suitable manner if necessary, and stored in computer memory.

The foregoing detailed description of one or more embodiments of the approach for providing medically imaging compatible, radiolucent actuation, translation, rotation, articulation, and circumduction of patient platforms, anatomic positioners, surgical robotics, and surgical robotic end effectors within the medical imaging environment. It will be recognized that there are advantages to certain individual features and functions described herein that may be obtained without incorporating other features and functions described herein. Moreover, it will be recognized that various alternatives, modifications, variations, or improvements of the above-disclosed embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the embodiments contained herein.

What is claimed is:

1. A Joint for use in a surgical device, comprising:
a rhomboidal shaped member having a first surface and a second surface movably secured in a first support;
a first pneumatic bag in contact with the first surface of the rhomboidal shape; and
a second pneumatic bag in contact with the second surface of the rhomboidal shape, where the first pneumatic bag is filled inversely to the second pneumatic bag being emptied resulting in the rhomboidal shaped member moving in a first plane about a central pivot point.

2. The joint for use in a surgical device of claim 1, where the rhomboidal shaped member, first pneumatic bag, and second pneumatic bag are radiolucent.

3. The joint for use in a surgical device of claim 1, includes a cable that that when secured acts as a break to stop movement of rhomboidal shaped member.

4. The joint for use in a surgical device of claim 1, including:
a third pneumatic bag; and
a fourth pneumatic bag that is filled inversely to the third pneumatic bag being emptied in a second support, with the third pneumatic bag and fourth pneumatic bag acting on the first support resulting in movement of the rhomboidal shaped member in a second plane about the central pivot point.

5. The joint for use in a surgical device of claim 4, where the joint is radiolucent.

6. The joint for use in a surgical device of claim 4, including:
a fifth pneumatic bag; and
a sixth pneumatic bag that is filled inversely to the third pneumatic bag being emptied in a fifth support acting on the second support resulting in the movement of the rhomboidal shaped member in a third plain about the central pivot point.

7. The joint for use in a surgical device of claim 6, where the joint is radiolucent.

8. The joint for use in a surgical device of claim 6, where the filling and emptying of all of the pneumatic bags is controlled from a gesture podium that translates movement of a human joint to the joint via a controller that controls a plurality of valves on a manifold.

9. The joint for use in a surgical device of claim 4, where the joint is in a surgical robot.

10. The joint for use in a surgical device of claim 1, where filling and emptying of at least the first pneumatic bag and second pneumatic bag is controlled by activating at least a first valve on a manifold coupled to the first pneumatic bag and second pneumatic bag, where the at least a first valve is controlled by a controller.

* * * * *